United States Patent
Wang et al.

(10) Patent No.: US 9,624,180 B2
(45) Date of Patent: Apr. 18, 2017

(54) SQUARIC DERIVATIVES FOR THE TREATMENT OF HEPATITIS C

(71) Applicant: BRISTOL-MYERS SQUIBB COMPANY, Princeton, NJ (US)

(72) Inventors: Tao Wang, Farmington, CT (US); Zhongxing Zhang, Madison, CT (US); Paul Michael Scola, Glastonbury, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/762,554

(22) PCT Filed: Jan. 23, 2014

(86) PCT No.: PCT/US2014/012650
§ 371 (c)(1),
(2) Date: Jul. 22, 2015

(87) PCT Pub. No.: WO2014/116772
PCT Pub. Date: Jul. 31, 2014

(65) Prior Publication Data
US 2015/0322020 A1    Nov. 12, 2015

Related U.S. Application Data

(60) Provisional application No. 61/756,557, filed on Jan. 25, 2013.

(51) Int. Cl.
| | | |
|---|---|---|
| *C07D 251/52* | (2006.01) | |
| *A61K 31/53* | (2006.01) | |
| *C07D 403/12* | (2006.01) | |
| *A61P 31/14* | (2006.01) | |
| *A61K 45/06* | (2006.01) | |

(52) U.S. Cl.
CPC ............ *C07D 251/52* (2013.01); *A61K 31/53* (2013.01); *A61K 45/06* (2013.01); *C07D 403/12* (2013.01)

(58) Field of Classification Search
CPC ............................. C07D 251/52; A61K 31/53
USPC ................................... 544/208, 209; 514/245
See application file for complete search history.

(56) References Cited

U.S. PATENT DOCUMENTS 7,163,943 B2    1/2007    Timmer et al.
8,445,490 B2    5/2013    Wang et al.

FOREIGN PATENT DOCUMENTS

EP    1 674 457 A1    6/2006

OTHER PUBLICATIONS

PubChem Database pccompound-1, Aug. 4, 2016; Create Date Jul. 2005.*
PubChem Database pccompound-2, Aug. 4, 2016; Create Date Jul. 2005 to Nov. 2012.*

* cited by examiner

*Primary Examiner* — Venkataraman Balasubramanian
(74) *Attorney, Agent, or Firm* — John F. Levis

(57) ABSTRACT

Compounds of Formula I, including pharmaceutically acceptable salts thereof, are set forth, in addition to compositions and methods of using these compounds. The compounds have activity against hepatitis C virus (HCV) and may be useful in treating those infected with HCV.

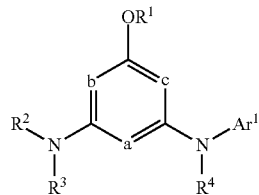

7 Claims, No Drawings

SQUARIC DERIVATIVES FOR THE TREATMENT OF HEPATITIS C

CROSS REFERENCE TO RELATED APPLICATION

This application claims the priority of U.S. provisional application Ser. No. 61/756,557 filed Jan. 25, 2013 which is herein incorporated by reference.

FIELD OF THE INVENTION

The invention relates to novel compounds of Formula I, including pharmaceutically acceptable salts thereof, which have activity against hepatitis C virus (HCV), and are useful in treating those infected with HCV. The invention also relates to compositions and methods of using these compounds.

BACKGROUND OF THE INVENTION

Hepatitis C virus (HCV) chronically infects an estimated 170 million people worldwide, with 3 to 4 million infected individuals in the United States alone (Boyer, N. and Marcellin, P. *J. Hepatology.* 2000, 32:98-112; Alter, M. J., et al. *Engl. J. Med.* 1999, 341:556-562). Prior to the mid 1990s, transfusion with infected blood products was the main route of HCV transmission. Following the introduction of blood screening methods, transmission via injection drug use became the primary risk factor. Chronic infection often leads to the development of severe liver complications, including fibrosis, cirrhosis, and hepatocellular carcinoma. HCV infection is also the leading cause of orthotopic liver transplantation in the United States. The degree to which disease progression is related to viral and cellular factors is not completely understood.

Considerable heterogeneity is found within the nucleotide and encoded amino acid sequence of the HCV genome (Simmonds, P. *J. Gen. Virology.* 2004, 85:3173-3188). Based on this sequence diversity, six major genotypes and multiple associated subtypes have been described. The genotypes of HCV differ in their worldwide distribution, and the clinical significance of the genetic heterogeneity of HCV remains elusive despite numerous studies of the possible effect of genotypes on pathogenesis and therapy.

Medical treatment for HCV is limited by the lack of a vaccine or approved therapies that specifically target the virus. Currently, patients undergo treatment with a combination of parenterally administered pegylated alpha-interferon and oral ribavirin. Genotype 1 HCV is the most difficult to treat and elimination of the virus (sustained virologic response) is achieved for only approximately 50% of patients (Fried, M. W. et al. *N. Engl. J. Med.* 2002, 347:975-982; Zeumzem, S. *Nature Clinical Practice.* 2008, 5:610-622). This poor treatment response, combined with often severe side effects induced by therapy, highlight a need for improved antiviral drugs with better efficacy and safety profiles.

HCV is a member of the Flaviviridae family of viruses with a single-stranded positive-sense RNA genome. Following infection of host cells, the 9.6 Kb genome is translated into a polyprotein precursor of approximately 3,000 amino acids (reviewed in Lindenbach, B. D. and Rice, C. M. *Nature.* 2005, 436:933-938; Moradpour, D, Penin, F., and Rice, C. M. *Nature Reviews.* 2007, 5:453-463). Post-translational processing by both cellular and viral proteases results in the generation of at least 10 separate viral proteins.

The structural proteins (which by definition are found in mature virions) include core, E1, E2, and possibly p7, and originate from the amino-terminal region of the polyprotein. The core protein assembles into the viral nucleocapsid. The E1 and E2 glycoproteins form heterodimers that are found within the lipid envelope surrounding the viral particles, and mediate host cell receptor binding and entry of the virus into cells. It is unclear if p7 is a structural protein, and its role in replication has yet to be defined. However p7 is believed to form an ion channel in cellular membranes, preventing acidification of intracellular compartments in which virions are assembled, and it has been shown to be essential for viral replication and assembly. The nonstructural proteins NS2, NS3, NS4A, NS4B, NS5A, and NS5B are produced through maturational cleavages of the carboxy-terminal region of the polyprotein. NS2 along with the amino terminus of NS3 form the NS2-3 metalloprotease which cleaves at the NS2-NS3 junction. Additionally, NS2 is involved in assembly and egress of nascent virions. The NS3 protein contains both a serine protease in its amino-terminal region, and a nucleotide-dependent RNA helicase in its carboxy-terminal region. NS3 forms a heterodimer with the NS4A protein, constituting the active protease which mediates cleavages of the polyprotein downstream of NS3, both in cis, at the NS3-NS4A cleavage site, and in trans, for the remaining NS4A-NS4B, NS4B-NS5A, NS5A-NS5B sites. The complex formation of the NS3 protein with NS4A seems necessary to the processing events, enhancing the proteolytic efficiency at all of the sites. The NS3 protein also exhibits nucleoside triphosphatase and RNA helicase activities. The NS4B protein has been shown to be important for localization of HCV proteins into replication complexes in altered membranous structures within the cell. NS5B encodes an RNA-dependent RNA polymerase that is involved in the replication of HCV.

Subgenomic HCV replicons, containing the untranslated regions 5' and 3' to the coding sequence fused to the nonstructural proteins or the full-length polyprotein, are competent for translation, viral protein expression, and replication within cultured cells (Lohmann, V. et al. *Science.* 1999, 285:110-113; Moradpour, D, Penin, F., and Rice, C. M. *Nature Reviews.* 2007, 5:453-463). The replicon system has proven valuable for the identification of inhibitors targeting the nonstructural proteins associated with these functions. However, only limited subsets of HCV genotypes have been used to generate functional replicons.

Other systems have been used to study the biology of the HCV structural proteins that mediate the entry into host cells. For example, virus-like-particles made in recombinant baculovirus-infected cells with the HCV core, E1 and E2 proteins have also been used to study the function of the HCV E1 and E2 proteins (Barth, H., et al. *J. Biol. Chem.* 2003, 278:41003-41012). In addition, pseudotyping systems where the E1 and E2 glycoproteins are used to functionally replace the glycoproteins of retroviruses have been developed (Bartosch, B., Dubuisson, J. and Cosset, F.-L. *J. Exp. Med.* 2003, 197:633-642; Hsu, M. et al. *Proc. Natl. Acad. Sci. USA.* 2003, 100:7271-7276). These systems yield HCV pseudoparticles that bind to and enter host cells in a manner which is believed to be analogous to the natural virus, thus making them a convenient tool to study the viral entry steps as well as to identify inhibitors block this process.

Recently, a full-length genotype 2a HCV clone, JFH1, was isolated and demonstrated the ability to replicate in vitro. Through repeated passage and adaptation in cell culture increased titers of infectious virus were produced (Lindenbach, B. D., et al. *Science.* 2005, 309:623-626; Wakita, T. et al. *Nature Med.* 2005, 11:791-796). In contrast to the HCV replicon or pseudotyping systems, the infectious virus is useful for studying the complete HCV replication cycle, including identifying inhibitors of not only the replication proteins, but those involved in early steps in virus infection (entry and uncoating) and production of progeny viruses (genome packaging, nucleocapsid assembly, virion envelopment and egress).

Triazines have been disclosed. See WO 2009/091388 and US 2009/0286778.

The invention provides technical advantages, for example, the compounds are novel and are effective against hepatitis C. Additionally, the compounds provide advantages for pharmaceutical uses, for example, with regard to one or more of their mechanism of action, binding, inhibition efficacy, target selectivity, solubility, safety profiles, or bioavailability.

SUMMARY OF THE INVENTION

One aspect of the invention is a compound of Formula I, including pharmaceutically acceptable salts thereof:

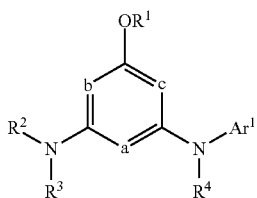

wherein
a, b and c are nitrogen;
or a and b are nitrogen, while c is —CH;
or b and c are nitrogen, while a is —CH;
or a and c are nitrogen, while b is —CH;
$R^1$ is selected from alkyl, hydroxyalkyl, alkoxyalkyl, haloalkyl, cycloalkyl, hydroxycycloalkyl, alkoxycycloalkyl, halocycloalkyl, cycloalkenyl, indanyl, alkylcarbonyl, and benzyl, wherein the benzyl moiety is substituted with 0-3 substituents selected from halo, alkyl, cycloalkyl, alkenyl, alkynyl, hydroxyl, cyano, haloalkyl, alkoxy, and haloalkoxy;
$R^2$ is selected from alkyl, cycloalkyl, $(Ar^2)$alkyl, $(Ar^2)$cycloalkyl, $((Ar^2)$cycloalkyl)alkyl, $((Ar^2)$alkyl)cycloalkyl, and $(((Ar^2)$alkyl)cycloalkyl)alkyl;
$R^3$ is hydrogen, alkyl or cycloalkyl;
$R^4$ is hydrogen, alkyl or cycloalkyl;
$R^5$ is

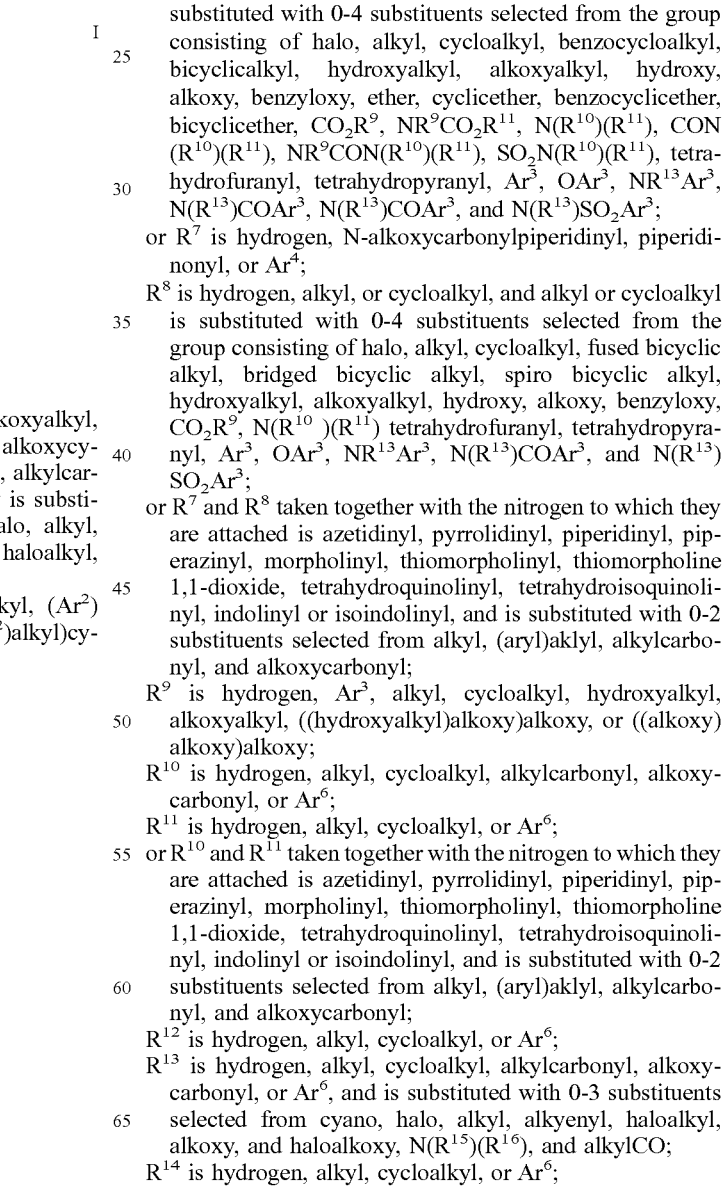

wherein ring A is a 4 to 7 membered alkylene ring substituted with L;
$R^6$ is selected from hydrogen, halo, alkyl, cycloalkyl, haloalkyl, halocycloalkyl, alkoxy, and haloalkoxy;
$R^7$ is hydroxy, alkyloxy, phenoxy, $SO_2R^9$, $SO_2N(R^{10})(R^{11})$, CN, alkyl, cycloalkyl, benzocycloalkyl, bicyclicalkyl, (cycloalkyl)alkyl, (alkyl)cycloalkyl, ((alkyl))cycloalkyl)alkyl, or bridged bicycloalkyl, and is substituted with 0-4 substituents selected from the group consisting of halo, alkyl, cycloalkyl, benzocycloalkyl, bicyclicalkyl, hydroxyalkyl, alkoxyalkyl, hydroxy, alkoxy, benzyloxy, ether, cyclicether, benzocyclicether, bicyclicether, $CO_2R^9$, $NR^9CO_2R^{11}$, $N(R^{10})(R^{11})$, $CON(R^{10})(R^{11})$, $NR^9CON(R^{10})(R^{11})$, $SO_2N(R^{10})(R^{11})$, tetrahydrofuranyl, tetrahydropyranyl, $Ar^3$, $OAr^3$, $NR^{13}Ar^3$, $N(R^{13})COAr^3$, $N(R^{13})COAr^3$, and $N(R^{13})SO_2Ar^3$;
or $R^7$ is hydrogen, N-alkoxycarbonylpiperidinyl, piperidinonyl, or $Ar^4$;
$R^8$ is hydrogen, alkyl, or cycloalkyl, and alkyl or cycloalkyl is substituted with 0-4 substituents selected from the group consisting of halo, alkyl, cycloalkyl, fused bicyclic alkyl, bridged bicyclic alkyl, spiro bicyclic alkyl, hydroxyalkyl, alkoxyalkyl, hydroxy, alkoxy, benzyloxy, $CO_2R^9$, $N(R^{10})(R^{11})$ tetrahydrofuranyl, tetrahydropyranyl, $Ar^3$, $OAr^3$, $NR^{13}Ar^3$, $N(R^{13})COAr^3$, and $N(R^{13})SO_2Ar^3$;
or $R^7$ and $R^8$ taken together with the nitrogen to which they are attached is azetidinyl, pyrrolidinyl, piperidinyl, piperazinyl, morpholinyl, thiomorpholinyl, thiomorpholine 1,1-dioxide, tetrahydroquinolinyl, tetrahydroisoquinolinyl, indolinyl or isoindolinyl, and is substituted with 0-2 substituents selected from alkyl, (aryl)aklyl, alkylcarbonyl, and alkoxycarbonyl;
$R^9$ is hydrogen, $Ar^3$, alkyl, cycloalkyl, hydroxyalkyl, alkoxyalkyl, ((hydroxyalkyl)alkoxy)alkoxy, or ((alkoxy)alkoxy)alkoxy;
$R^{10}$ is hydrogen, alkyl, cycloalkyl, alkylcarbonyl, alkoxycarbonyl, or $Ar^6$;
$R^{11}$ is hydrogen, alkyl, cycloalkyl, or $Ar^6$;
or $R^{10}$ and $R^{11}$ taken together with the nitrogen to which they are attached is azetidinyl, pyrrolidinyl, piperidinyl, piperazinyl, morpholinyl, thiomorpholinyl, thiomorpholine 1,1-dioxide, tetrahydroquinolinyl, tetrahydroisoquinolinyl, indolinyl or isoindolinyl, and is substituted with 0-2 substituents selected from alkyl, (aryl)aklyl, alkylcarbonyl, and alkoxycarbonyl;
$R^{12}$ is hydrogen, alkyl, cycloalkyl, or $Ar^6$;
$R^{13}$ is hydrogen, alkyl, cycloalkyl, alkylcarbonyl, alkoxycarbonyl, or $Ar^6$, and is substituted with 0-3 substituents selected from cyano, halo, alkyl, alkyenyl, haloalkyl, alkoxy, and haloalkoxy, $N(R^{15})(R^{16})$, and alkylCO;
$R^{14}$ is hydrogen, alkyl, cycloalkyl, or $Ar^6$;

or $R^{13}$ and $R^{14}$ taken together with the nitrogen to which they are attached is azetidinyl, pyrrolidinyl, piperidinyl, piperazinyl, morpholinyl, thiomorpholinyl, thiomorpholine 1,1-dioxide, tetrahydroquinolinyl, tetrahydroisoquinolinyl, indolinyl, or isoindolinyl, and is substituted with 0-2 substituents selected from alkyl, (aryl)aklyl, alkylcarbonyl, and alkoxycarbonyl;

$R^{15}$ is hydrogen, alkyl, cycloalkyl, alkylcarbonyl, or alkoxycarbonyl;

$R^{16}$ is hydrogen, alkyl, or cycloalkyl;

or $R^{15}$ and $R^{16}$ taken together with the nitrogen to which they are attached is azetidinyl, pyrrolidinyl, piperidinyl, piperazinyl, morpholinyl, thiomorpholinyl, thiomorpholine 1,1-dioxide, tetrahydroquinolinyl, tetrahydroisoquinolinyl, indolinyl, or isoindolinyl, and is substituted with 0-2 substituents selected from alkyl, (aryl)aklyl, alkylcarbonyl, and alkoxycarbonyl;

L is selected from the group of alkylene, cycloalkylene, (cycloalkyl)alkyl, (alkyl)cycloalkyl, and alkyl(cycloalkyl)alkyl, and is substituted with 0-1$CO_2R^{12}$ or $CONR^{13}R^{14}$;

$Ar^1$ is phenyl or pyridyl or pyrimidinyl or pyrazolyl, substituted with 1$CON(R^5)(R^6)$, $OR^5$, $N(R^5)(R^6)$ or $R^5$, or with 0-3 substituents selected from halo, alkyl, haloalkyl, alkoxy, and haloalkoxy;

$Ar^2$ is phenyl substituted with 0-3 substituents selected from halo, hydroxy, cyano, alkyl, cycloalkyl, alkenyl, alkynyl, haloalkyl, alkoxy, and haloalkoxy;

$Ar^3$ is phenyl, biphenyl, terphenyl, naphthalenyl, furanyl, benzofuranyl, fluorenyl, fluorenonyl, thiophenyl, benzothiophenyl, pyrrolyl, indolyl, indanyl, pyridinyl, quinolinyl, azaquinolinyl, isoquinolinyl, azaisoquinolinyl, quinoxalinyl, azaquinoxalinyl, pyrimidinyl, quinazolinyl, azaquinazolinyl, pyrazolyl, indazolyl, azaindolyl, oxazolyl, benzoxazolyl, azabenzoxazolyl, isoxazolyl, benzoisoxazolyl, azabenzoisoxazolyl, imidazolyl, benzoimidazolyl, azabenzoimidazolyl, thiazolyl, benzothiazolyl, azabenzothiazolyl, isothiazolyl, benzoisothiazolyl, azabenzoisothiazolyl, oxadiazolyl, thiadiazolyl, triazolyl, benzotriazolyl, azabenzotriazolyl, tetrazolyl, indolinyl, chromenonyl, or dibenzofuranyl, and is substituted with 0-5 substituents selected from cyano, halo, alkyl, cycloalkyl, alkenyl, alkynyl, haloalkyl, cycloalkyl, $(CO_2R^{12})$alkyl, $(CO_2R^{12})$alkenyl,) $CON(R^{13})(R^{14})$alkyl, phenyl, hydroxy, alkoxy, $Ar^5$, $OAr^5$, $NR^{13}$, $Ar^5$, $N(R^{13})COAr^5$, $N(R^{13})SO_2Ar^5$, alkylthio, haloalkoxy, haloalkylthio, alkylcarbonyl, $CO_2R^{12}$, $COR^{12}$, $SO_2R^{12}$, $CON(R^{13})(R^{14})$, $SO_2N(R^{13})(R^{14})$, $N(R^{13})(R^{14})$, amidine, urea, ketone, sulfone, sulfamide, and $PhCONHSO_2$; and said alkyl, alkenyl, cycloalkyl, alkynyl or $Ar^5$ is further substituted with 0-5 substituents selected from cyano, halo, alkyl, cycloalkyl, alkenyl, alkynyl, haloalkyl, cycloalkyl, $(CO_2R^{12})$alkyl, $(CO_2R^{12})$alkenyl, $(CON(R^{13})(R^{14}))$alkyl, phenyl, hydroxy, alkoxy, aryoxy, alkylthio, haloalkoxy, haloalkylthio, alkylcarbonyl, $CO_2R^{12}$, $COR^{12}$, $SO_2R^{12}$, $CON(R^{13})(R^{14})$, $SO_2N(R^{13})(R^{14})$, $N(R^{13})(R^{14})$, amidine, urea, ketone, sulfone, sulfamide, $PhCONHSO_2$ and $Ar^6$;

or $Ar^3$ is phenyl substituted with 1 substituents selected from benzyl, phenoxy, pyridyloxy, pyrimidyloxy, tetrazolyloxy, thiazolyl, phenylpyrazolyl, methyloxadiazolyl, thiadiazolyl, triazolyl, methyltriazolyl, tetrazolyl, pyridinyl, dimethoxypyrimdinyl, indolyl, indolinyl, and isoindolinyl;

$Ar^4$ is phenyl, indanyl, tetrahydronaphthyl, isochromanyl, benzodioxolyl, pyridinyl, pyrazolyl, imidazolyl, or triazolyl, and is substituted with 0-3 substituents selected from cyano, halo, alkyl, alkyenyl, haloalkyl, alkoxy, and haloalkoxy, $N(R^{13})(R^{14})$, and alkylCO;

$Ar^5$ is phenyl, naphthalenyl, furanyl, benzofuranyl, azabenzofuranyl, thiophenyl, benzothiophenyl, azabenzothiophenyl, pyrrolyl, indolyl, azaindolyl, indanyl, pyridinyl, quinolinyl, azaquinolinyl, isoquinolinyl, azaisoquinolinyl, quinoxalinyl, azaquinoxalinyl, pyrimidinyl, quinazolinyl, azaquinazolinyl, pyrazolyl, indazolyl, azaindazolyl, oxazolyl, benzoxazolyl, azabenzoxazolyl, isoxazolyl, benzoisoxazolyl, azabenzoisoxazolyl, imidazolyl, benzoimidazolyl, azabenzoimidazolyl, thiazolyl, benzothiazolyl, azabenzothiazolyl, isothiazolyl, benzoisothiazolyl, azabenzothiazolyl, oxadiazolyl, thiadiazolyl, triazolyl, benzotriazolyl, azabenzotriazolyl, tetrazolyl, or indolinyl, and is substituted with 0-5 substituents selected from cyano, halo, alkyl, cycloalkyl, alkenyl, alkynyl, haloalkyl, cycloalkyl, $(CO_2R^{12})$alkyl, $(CO_2R^{12})$alkenyl, $(CON(R^{13})(R^{14}))$alkyl, phenyl, hydroxy, alkoxy, $OAr^6$, $NR^{13}Ar^6$, alkylthio, haloalkoxy, haloalkylthio, alkylcarbonyl, $CO_2R^{12}$, $COR^{12}$, $SO_2R^{12}$, $CON(R^{13})(R^{14})$, $SO_2N(R^{13})(R^{14})$, $N(R^{13})(R^{14})$ amidine, urea, ketone, sulfone and sulfamide;

$Ar^6$ is phenyl, naphthalenyl, furanyl, benzofuranyl, azabenzofuranyl, thiophenyl, benzothiophenyl, azabenzothiophenyl, pyrrolyl, indolyl, azaindolyl, indanyl, pyridinyl, quinolinyl, azaquinolinyl, isoquinolinyl, azaisoquinolinyl, quinoxalinyl, azaquinoxalinyl, pyrimidinyl, quinazolinyl, azaquinazolinyl, pyrazolyl, indazolyl, azaindazolyl, oxazolyl, benzoxazolyl, azabenzoxazolyl, isoxazolyl, benzoisoxazolyl, azabenzoisoxazolyl, imidazolyl, benzoimidazolyl, azabenzoimidazolyl, thiazolyl, benzothiazolyl, azabenzothiazolyl, isothiazolyl, benzoisothiazolyl, azabenzothiazolyl, oxadiazolyl, thiadiazolyl, triazolyl, benzotriazolyl, azabenzotriazolyl, tetrazolyl, or indolinyl, and is substituted with 0-5 substituents selected from cyano, halo, alkyl, cycloalkyl, alkenyl, alkynyl, haloalkyl, cycloalkyl, phenyl, hydroxy, alkoxy, aryloxy, alkylthio, haloalkoxy, haloalkylthio, alkylcarbonyl, ester, ketone, amidine, urea, ketone, sulfone and sulfamide;

The invention also relates to pharmaceutical compositions comprising a compound of Formula 1, including a pharmaceutically acceptable salt thereof, and a pharmaceutically acceptable carrier.

In addition, the invention provides one or more methods of treating hepatitis C infection comprising administering a therapeutically effective amount of a compound of Formula I to a patient.

Also provided as part of the invention are one or more methods for making the compounds of Formula I.

The present invention is directed to these, as well as other important ends, hereinafter described.

DETAILED DESCRIPTION OF THE EMBODIMENTS

Unless otherwise specifically set forth elsewhere in the application, these terms have the following meanings. "H" refers to hydrogen, including its isotopes, such as deuterium. "Halo" means fluoro, chloro, bromo, or iodo. "Alkyl" means a straight or branched alkyl group composed of 1 to 6 carbons. "Alkenyl" means a straight or branched alkyl group composed of 2 to 6 carbons with at least one double bond. "Cycloalkyl" means a monocyclic ring system composed of 3 to 8 carbons. "Alkylene" means a straight or branched divalent alkyl group. "Alkenylene" means a straight or branched divalent alkyl group with at least one double bond. "Cycloalkylene" means a divalent cycloalkane moiety composed of 3 to 7 carbons and includes gem-divalency (for example 1,1-cyclopropanediyl) as well as non-gem-divalency (for example, 1,4-cyclohexanediyl). "Alkylidinyl" means a divalent alkene substituent where the divalency occurs on the same carbon of the alkene. "Hydroxyalkyl," "alkoxy" and other terms with a substituted alkyl moiety include straight and branched isomers composed of 1 to 6 carbon atoms for the alkyl moiety. "Haloalkyl" and "haloalkoxy" include all halogenated isomers from monohalo substituted alkyl to perhalo substituted alkyl. "Aryl" includes carbocyclic and heterocyclic aromatic substituents. Phenylene is a divalent benzene ring. "1,4-Phenylene" means 1,4-benzenediyl with respect to regiochemistry for the divalent moiety. Parenthetic and multiparenthetic terms are intended to clarify bonding relationships to those skilled in the art. For example, a term such as ((R)alkyl) means an alkyl substituent further substituted with the substituent R.

The substituents described above may be attached at any suitable point of attachment unless otherwise specified. However, it is understood that the compounds encompassed by the present invention are those that are chemically stable as understood by those skilled in the art. Additionally, the compounds encompassed by the present disclosure are those that are suitably stable for use as a pharmaceutical agent.

As set forth above, the invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, camsylate, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention possess asymmetric carbon atoms (see, for example, the structures below). The invention includes all stereoisomeric forms, including enantiomers and diastereomers as well as mixtures of stereoisomers such as racemates. Some stereoisomers can be made using methods known in the art. Stereoisomeric mixtures of the compounds and related intermediates can be separated into individual isomers according to methods commonly known in the art. The use of wedges or hashes in the depictions of molecular structures in the following schemes and tables is intended only to indicate relative stereochemistry, and should not be interpreted as implying absolute stereochemical assignments.

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

As set forth above, the invention is directed to compounds of Formula I, including pharmaceutically acceptable salts thereof:

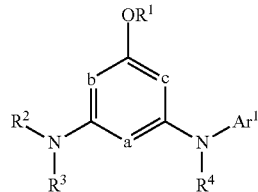

I wherein
a, b and c are nitrogen;
or a and b are nitrogen, while c is —CH;
or b and c are nitrogen, while a is —CH;
or a and c are nitrogen, while b is —CH;
$R^1$ is selected from alkyl, hydroxyalkyl, alkoxyalkyl, haloalkyl, cycloalkyl, hydroxycycloalkyl, alkoxycycloalkyl, halocycloalkyl, cycloalkenyl, indanyl, alkylcarbonyl, and benzyl, wherein the benzyl moiety is substituted with 0-3 substituents selected from halo, alkyl, cycloalkyl, alkenyl, alkynyl, hydroxyl, cyano, haloalkyl, alkoxy, and haloalkoxy;
$R^2$ is selected from alkyl, cycloalkyl, $(Ar^2)$alkyl, $(Ar^2)$cycloalkyl, $((Ar^2)$cycloalkyl)alkyl, $((Ar^2)$alkyl)cycloalkyl, and $(((Ar^2)$alkyl)cycloalkyl)alkyl;
$R^3$ is hydrogen, alkyl or cycloalkyl;
$R^4$ is hydrogen, alkyl or cycloalkyl;
$R^5$ is

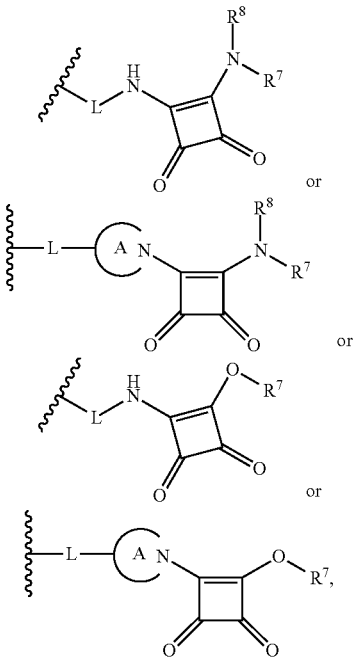

wherein ring A is a 4 to 7 membered alkylene ring substituted with L;

R⁶ is selected from hydrogen, halo, alkyl, cycloalkyl, haloalkyl, halocycloalkyl, alkoxy, and haloalkoxy;

R⁷ is hydroxy, alkyloxy, phenoxy, SO₂R⁹, SO₂N(R¹⁰)(R¹¹), CN, alkyl, cycloalkyl, benzocycloalkyl, bicyclicalkyl, (cycloalkyl)alkyl, (alkyl)cycloalkyl, ((alkyl))cycloalkyl, subalkyl, or bridged bicycloalkyl, and is substituted with 0-4 substituents selected from the group consisting of halo, alkyl, cycloalkyl, benzocycloalkyl, bicyclicalkyl, hydroxyalkyl, alkoxyalkyl, hydroxy, alkoxy, benzyloxy, ether, cyclicether, benzocyclicether, bicyclicether, CO₂R⁹, NR⁹CO₂R¹¹, N(R¹⁰)(R¹¹), CON(R¹⁰)(R¹¹), NR⁹CON(R¹⁰)(R¹¹), SO₂N(R¹⁰)(R¹¹), tetrahydrofuranyl, tetrahydropyranyl, Ar³, OAr³, NR¹³Ar³, N(R¹³)COAr³, N(R¹³)COAr³, and N(R¹³)SO₂Ar³;

or R⁷ is hydrogen, N-alkoxycarbonylpiperidinyl, piperidinonyl, or Ar⁴;

R⁸ is hydrogen, alkyl, or cycloalkyl, and alkyl or cycloalkyl is substituted with 0-4 substituents selected from the group consisting of halo, alkyl, cycloalkyl, fused bicyclic alkyl, bridged bicyclic alkyl, spiro bicyclic alkyl, hydroxyalkyl, alkoxyalkyl, hydroxy, alkoxy, benzyloxy, CO₂R⁹, N(R¹⁰)(R¹¹), tetrahydrofuranyl, tetrahydropyranyl, Ar³, OAr³, NR¹³Ar³, N(R¹³)COAr³, and N(R¹³)SO₂Ar³;

or R⁷ and R⁸ taken together with the nitrogen to which they are attached is azetidinyl, pyrrolidinyl, piperidinyl, piperazinyl, morpholinyl, thiomorpholinyl, thiomorpholine 1,1-dioxide, tetrahydroquinolinyl, tetrahydroisoquinolinyl, indolinyl or isoindolinyl, and is substituted with 0-2 substituents selected from alkyl, (aryl)aklyl, alkylcarbonyl, and alkoxycarbonyl;

R⁹ is hydrogen, Ar³, alkyl, cycloalkyl, hydroxyalkyl, alkoxyalkyl, ((hydroxyalkyl)alkoxy)alkoxy, or ((alkoxy)alkoxy)alkoxy;

R¹⁰ is hydrogen, alkyl, cycloalkyl, alkylcarbonyl, alkoxycarbonyl, or Ar⁶;

R¹¹ is hydrogen, alkyl, cycloalkyl, or Ar⁶;

or R¹⁰ and R¹¹ taken together with the nitrogen to which they are attached is azetidinyl, pyrrolidinyl, piperidinyl, piperazinyl, morpholinyl, thiomorpholinyl, thiomorpholine 1,1-dioxide, tetrahydroquinolinyl, tetrahydroisoquinolinyl, indolinyl or isoindolinyl, and is substituted with 0-2 substituents selected from alkyl, (aryl)aklyl, alkylcarbonyl, and alkoxycarbonyl;

R¹² is hydrogen, alkyl, cycloalkyl, or Ar⁶;

R¹³ is hydrogen, alkyl, cycloalkyl, alkylcarbonyl, alkoxycarbonyl, or Ar⁶, and is substituted with 0-3 substituents selected from cyano, halo, alkyl, alkyenyl, haloalkyl, alkoxy, and haloalkoxy, N(R¹⁵)(R¹⁶), and alkylCO;

R¹⁴ is hydrogen, alkyl, cycloalkyl, or Ar⁶;

or R¹³ and R¹⁴ taken together with the nitrogen to which they are attached is azetidinyl, pyrrolidinyl, piperidinyl, piperazinyl, morpholinyl, thiomorpholinyl, thiomorpholine 1,1-dioxide, tetrahydroquinolinyl, tetrahydroisoquinolinyl, indolinyl, or isoindolinyl, and is substituted with 0-2 substituents selected from alkyl, (aryl)aklyl, alkylcarbonyl, and alkoxycarbonyl;

R¹⁵ is hydrogen, alkyl, cycloalkyl, alkylcarbonyl, or alkoxycarbonyl;

R¹⁶ is hydrogen, alkyl, or cycloalkyl;

or R¹⁵ and R¹⁶ taken together with the nitrogen to which they are attached is azetidinyl, pyrrolidinyl, piperidinyl, piperazinyl, morpholinyl, thiomorpholinyl, thiomorpholine 1,1-dioxide, tetrahydroquinolinyl, tetrahydroisoquinolinyl, indolinyl, or isoindolinyl, and is substituted with 0-2 substituents selected from alkyl, (aryl)aklyl, alkylcarbonyl, and alkoxycarbonyl;

L is selected from the group of alkylene, cycloalkylene, (cycloalkyl)alkyl, (alkyl)cycloalkyl, and alkyl(cycloalkyl)alkyl, and is substituted with 0-1CO₂R¹² or CONR¹³R¹⁴;

Ar¹ is phenyl or pyridyl or pyrimidinyl or pyrazolyl, substituted with 1CON(R⁵)(R⁶), OR⁵, N(R⁵)(R⁶) or R⁵, or with 0-3 substituents selected from halo, alkyl, haloalkyl, alkoxy, and haloalkoxy;

Ar² is phenyl substituted with 0-3 substituents selected from halo, hydroxy, cyano, alkyl, cycloalkyl, alkenyl, alkynyl, haloalkyl, alkoxy, and haloalkoxy;

Ar³ is phenyl, biphenyl, terphenyl, naphthalenyl, furanyl, benzofuranyl, fluorenyl, fluorenonyl, thiophenyl, benzothiophenyl, pyrrolyl, indolyl, indanyl, pyridinyl, quinolinyl, azaquinolinyl, isoquinolinyl, azaisoquinolinyl, quinoxalinyl, azaquinoxalinyl, pyrimidinyl, quinazolinyl, azaquinazolinyl, pyrazolyl, indazolyl, azaindolyl, oxazolyl, benzoxazolyl, azabenzoxazolyl, isoxazolyl, benzoisoxazolyl, azabenzoisoxazolyl, imidazolyl, benzoimidazolyl, azabenzoimidazolyl, thiazolyl, benzothiazolyl, azabenzothiazolyl, isothiazolyl, benzoisothiazolyl, azabenzoisothiazolyl, oxadiazolyl, thiadiazolyl, triazolyl, benzotriazolyl, azabenzotriazolyl, tetrazolyl, indolinyl, chromenonyl, or dibenzofuranyl, and is substituted with 0-5 substituents selected from cyano, halo, alkyl, cycloalkyl, alkenyl, alkynyl, haloalkyl, cycloalkyl, (CO₂R¹²)alkyl, (CO₂R¹²)alkenyl, (CON(R¹³)(R¹⁴))alkyl, phenyl, hydroxy, alkoxy, Ar⁵, OAr⁵, NR¹³Ar⁵, N(R¹³)COAr⁵, N(R¹³)SO₂Ar⁵, alkylthio, haloalkoxy, haloalkylthio, alkylcarbonyl, CO₂R¹², COR¹², SO₂R¹², CON(R¹³)(R¹⁴), SO₂N(R¹³)(R¹⁴), N(R¹³)(R¹⁴), amidine, urea, ketone, sulfone, sulfamide, and PhCONHSO₂; and said alkyl, alkenyl, cycloalkyl, alkynyl or Ar⁵ is further substituted with 0-5 substituents selected from cyano, halo, alkyl, cycloalkyl, alkenyl, alkynyl, haloalkyl, cycloalkyl, (CO₂R¹²)alkyl, (CO₂R¹²)alkenyl, (CON(R¹³)(R¹⁴))alkyl, phenyl, hydroxy, alkoxy, aryoxy, alkylthio, haloalkoxy, haloalkylthio, alkylcarbonyl, CO₂R¹², COR¹², SO₂R¹², CON(R¹³)(R¹⁴), SO₂N(R¹³)(R¹⁴), N(R¹³)(R¹⁴), amidine, urea, ketone, sulfone, sulfamide, PhCONHSO₂ and Ar⁶;

or Ar³ is phenyl substituted with 1 substituent selected from benzyl, phenoxy, pyridyloxy, pyrimidyloxy, tetrazolyloxy, thiazolyl, phenylpyrazolyl, methyloxadiazolyl, thiadiazolyl, triazolyl, methyltriazolyl, tetrazolyl, pyridinyl, dimethoxypyrimdinyl, indolyl, indolinyl, and isoindolinyl;

Ar⁴ is phenyl, indanyl, tetrahydronaphthyl, isochromanyl, benzodioxolyl, pyridinyl, pyrazolyl, imidazolyl, or triazolyl, and is substituted with 0-3 substituents selected from cyano, halo, alkyl, alkyenyl, haloalkyl, alkoxy, and haloalkoxy, N(R¹³)(R¹⁴), and alkylCO;

Ar⁵ is phenyl, naphthalenyl, furanyl, benzofuranyl, azabenzofuranyl, thiophenyl, benzothiophenyl, azabenzothiophenyl, pyrrolyl, indolyl, azaindolyl, indanyl, pyridinyl, quinolinyl, azaquinolinyl, isoquinolinyl, azaisoquinolinyl, quinoxalinyl, azaquinoxalinyl, pyrimidinyl, quinazolinyl, azaquinazolinyl, pyrazolyl, indazolyl, azaindazolyl, oxazolyl, benzoxazolyl, azabenzoxazolyl, isoxazolyl, benzoisoxazolyl, azabenzoisoxazolyl, imidazolyl, benzoimidazolyl, azabenzoimidazolyl, thiazolyl, benzothiazolyl, azabenzothiazolyl, isothiazolyl, benzoisothiazolyl, azabenzoisothiazolyl, oxadiazolyl, thiadiazolyl, triazolyl, benzotriazolyl, azabenzotriazolyl, tetrazolyl, or indolinyl, and is substituted with 0-5 substituents selected from cyano, halo, alkyl, cycloalkyl, alkenyl, alkynyl, haloalkyl, cycloalkyl, (CO₂R¹²)alkyl, (CO₂R¹²)alkenyl, (CON(R¹³)(R¹⁴))alkyl, phenyl, hydroxy, alkoxy, OAr⁶, NR$^{13}$Ar$^6$, alkylthio, haloalkoxy, haloalkylthio, alkylcarbonyl, CO$_2$R$^{12}$, COR$^{12}$, SO$_2$R$^{12}$, CON(R$^{13}$)(R$^{14}$), SO$_2$N(R$^{13}$)(R$^{14}$), N(R$^{13}$)(R$^{14}$), amidine, urea, ketone, sulfone and sulfamide;

Ar$^6$ is phenyl, naphthalenyl, furanyl, benzofuranyl, azabenzofuranyl, thiophenyl, benzothiophenyl, azabenzothiophenyl, pyrrolyl, indolyl, azaindolyl, indanyl, pyridinyl, quinolinyl, azaquinolinyl, isoquinolinyl, azaisoquinolinyl, quinoxalinyl, azaquinoxalinyl, pyrimidinyl, quinazolinyl, azaquinazolinyl, pyrazolyl, indazolyl, azaindazolyl, oxazolyl, benzoxazolyl, azabenzoxazolyl, isoxazolyl, benzoisoxazolyl, azabenzoisoxazolyl, imidazolyl, benzoimidazolyl, azabenzoimidazolyl, thiazolyl, benzothiazolyl, azabenzothiazolyl, isothiazolyl, benzoisothiazolyl, azabenzothiazolyl, oxadiazolyl, thiadiazolyl, triazolyl, benzotriazolyl, azabenzotriazolyl, tetrazolyl, or indolinyl, and is substituted with 0-5 substituents selected from cyano, halo, alkyl, cycloalkyl, alkenyl, alkynyl, haloalkyl, cycloalkyl, phenyl, hydroxy, alkoxy, aryloxy, alkylthio, haloalkoxy, haloalkylthio, alkylcarbonyl, ester, ketone, amidine, urea, ketone, sulfone and sulfamide;

More preferred compounds, including pharmaceutically acceptable salts thereof, are selected from the group of

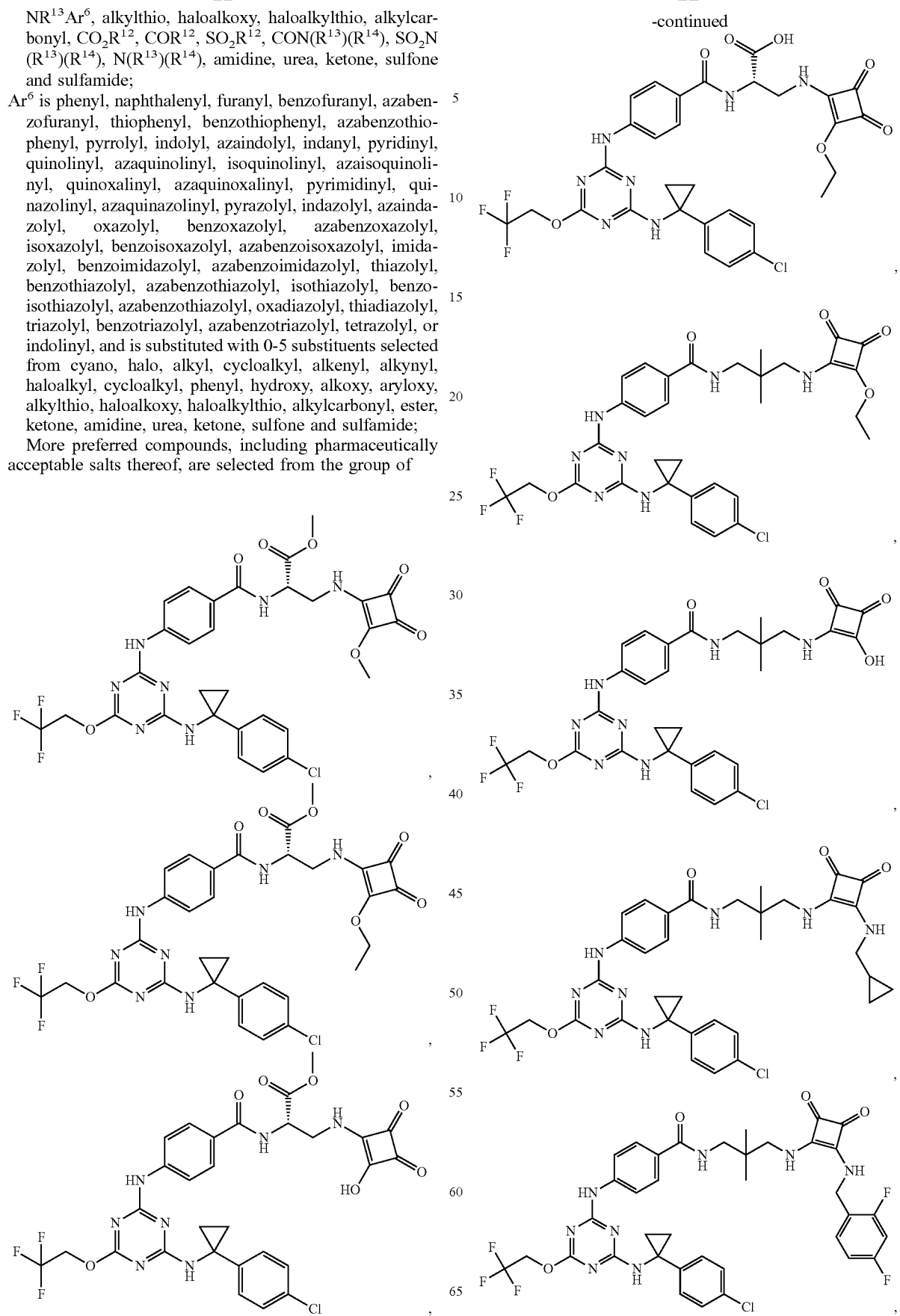

13
-continued
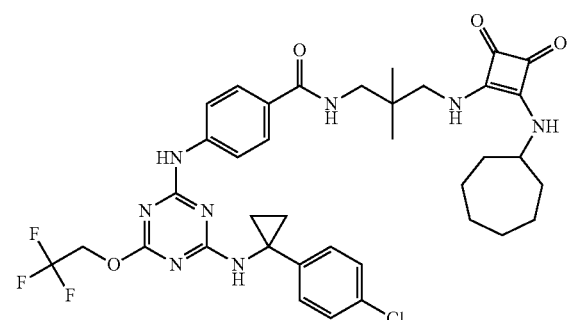
,
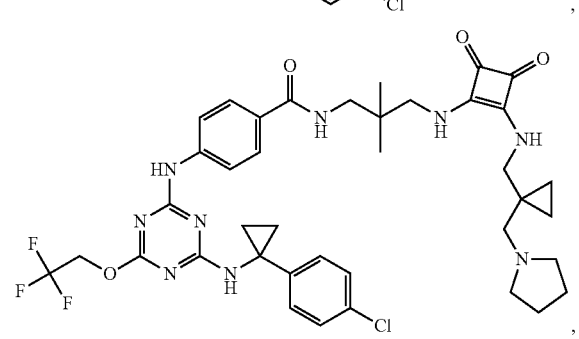
,
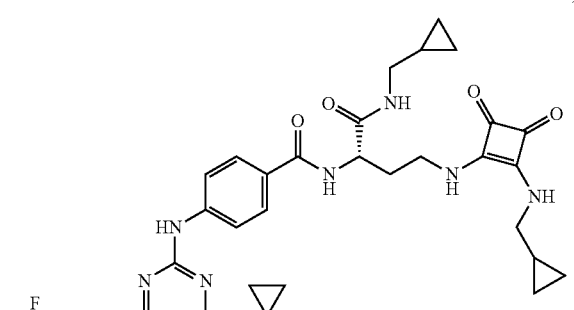
,
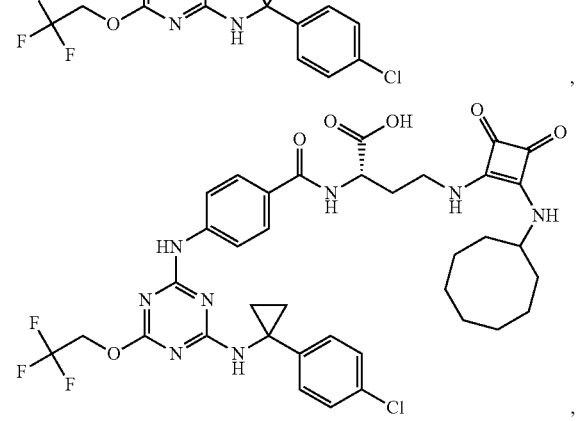
,
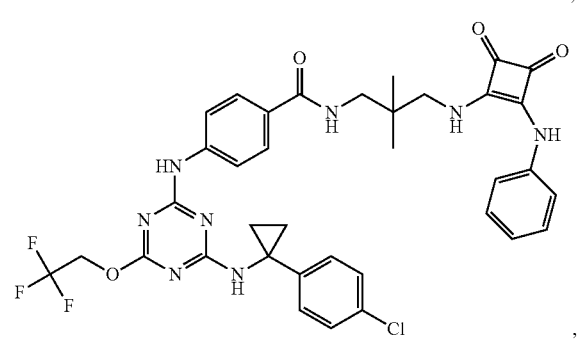
,
14
-continued
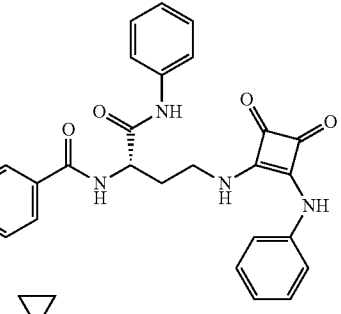
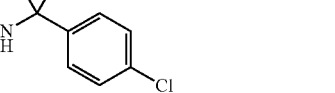
,
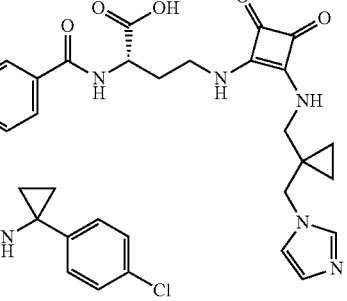
,
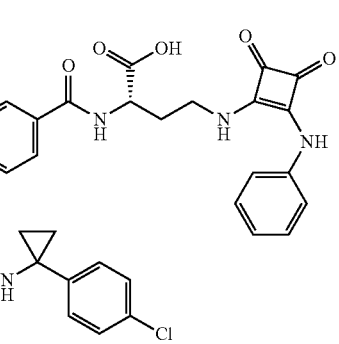
,
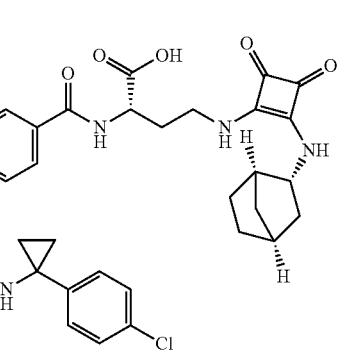
,

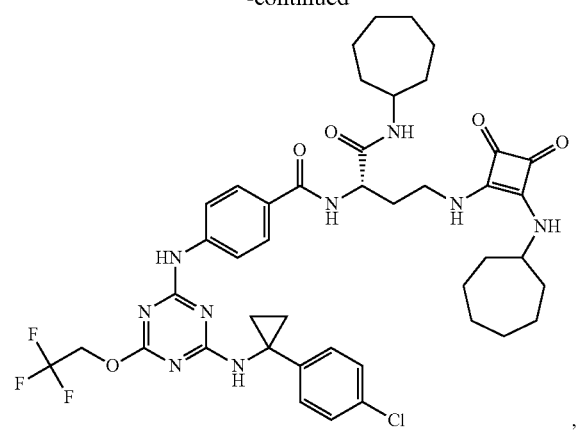
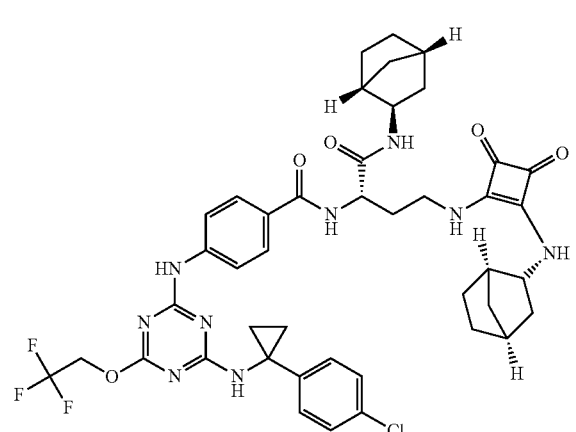
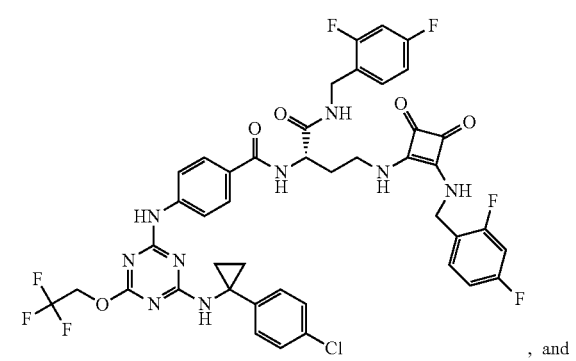
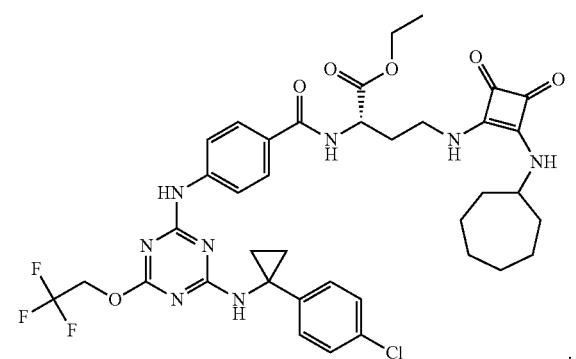 [SMILES: CCOC(=O)[C@H](CCNc1c(NC2CCCCCC2)c(=O)c1=O)NC(=O)c1ccc(Nc2nc(NC3(c4ccc(Cl)cc4)CC3)nc(OCC(F)(F)F)n2)cc1]
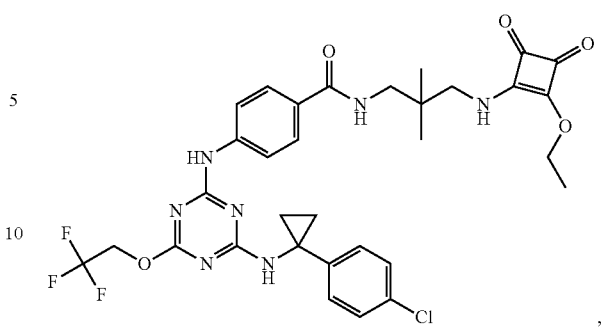
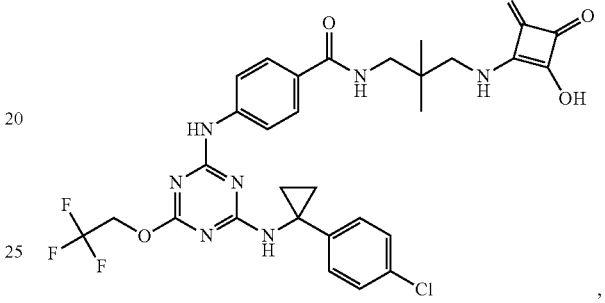
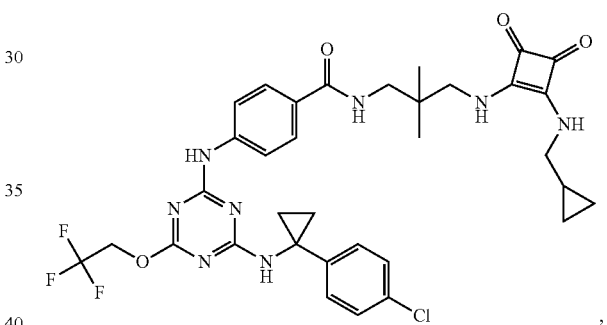
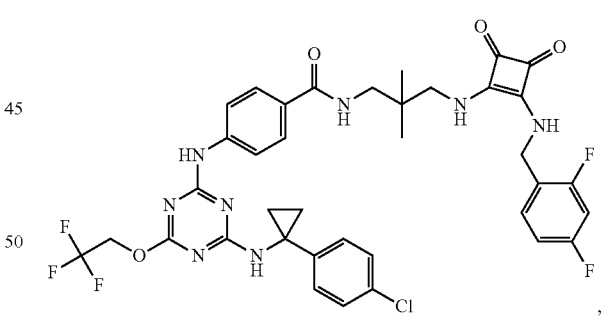
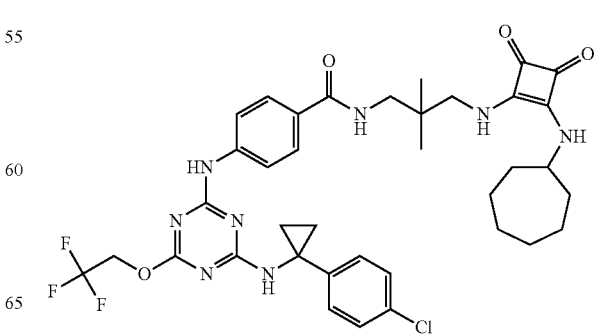
In addition, other preferred compounds, including pharmaceutically acceptable salts thereof, are selected from the group of 17
-continued
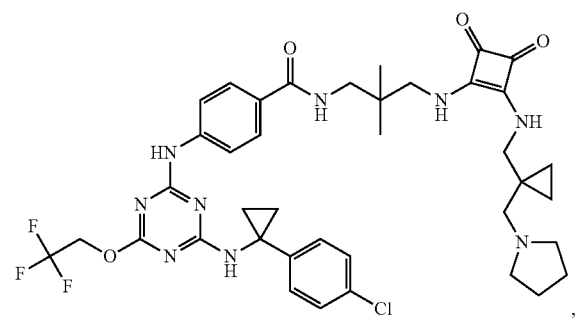
,
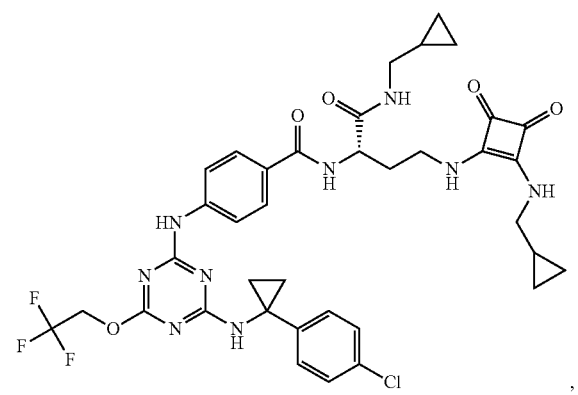
,
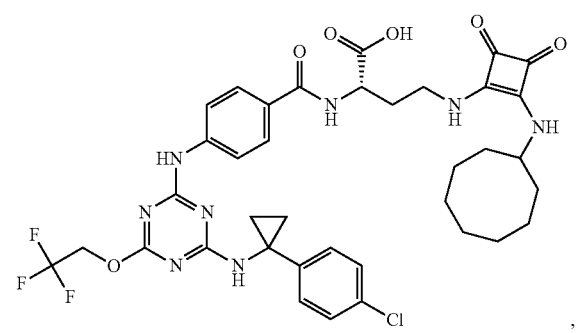
,
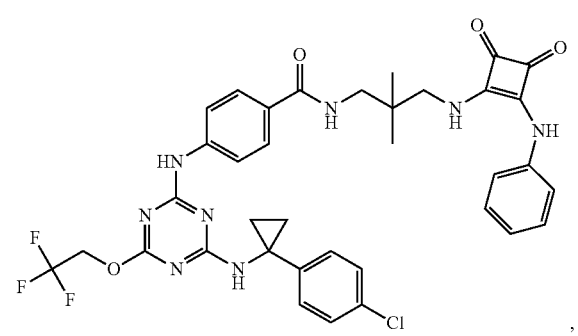
,
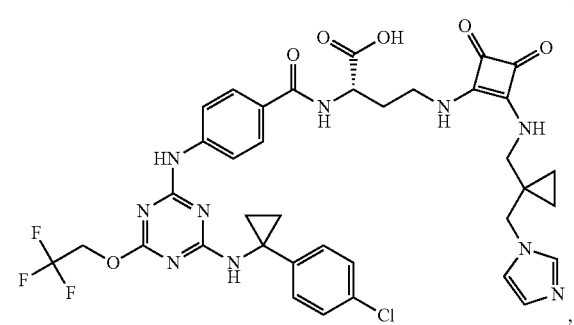
,
18
-continued
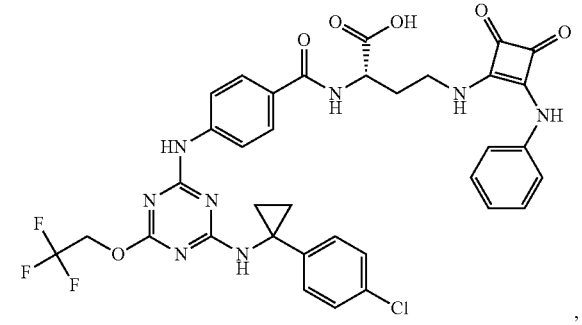
,
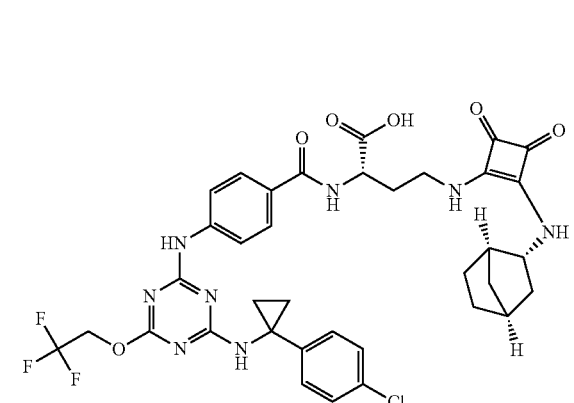
,
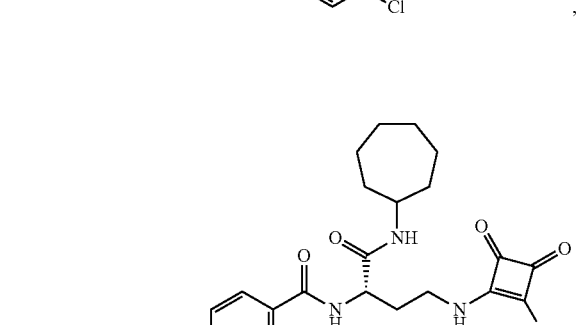
,
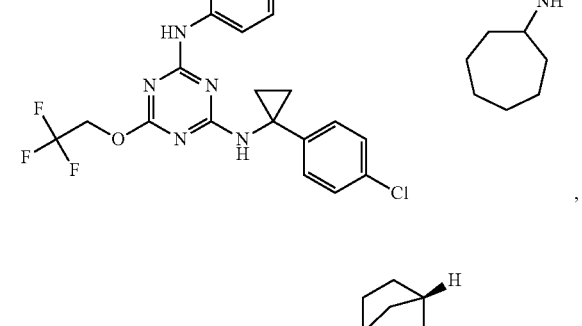
,
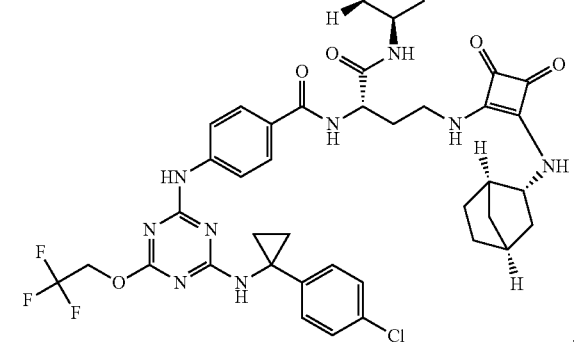
, -continued

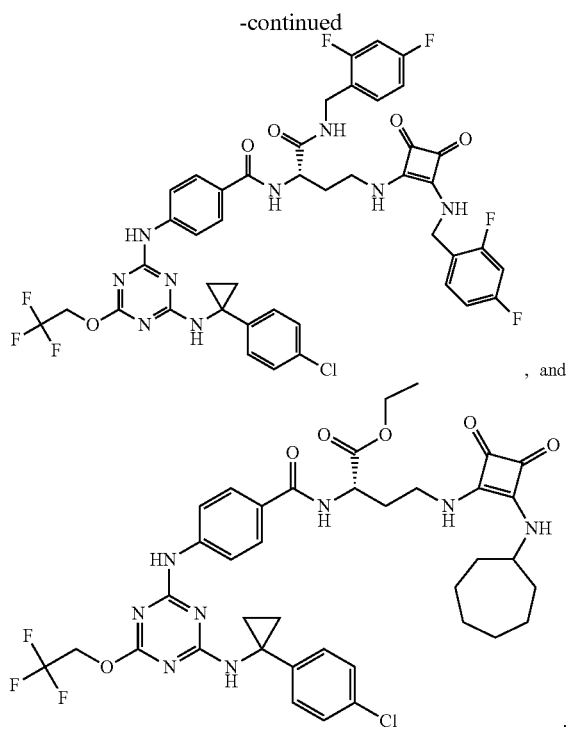

, and

Pharmaceutical Compositions and Methods of Treatment

The compounds demonstrate activity against HCV NS5B and can be useful in treating HCV and HCV infection. Therefore, another aspect of the invention is a composition comprising a compound, or a pharmaceutically acceptable salt thereof, and a pharmaceutically acceptable carrier.

Another aspect of the invention is a composition further comprising a compound having anti-HCV activity.

Another aspect of the invention is a composition where the compound having anti-HCV activity is an interferon or a ribavirin. Another aspect of the invention is where the interferon is selected from interferon alpha 2B, pegylated interferon alpha, consensus interferon, interferon alpha 2A, interferon lambda, and lymphoblastoid interferon tau.

Another aspect of the invention is a composition where the compound having anti-HCV activity is a cyclosporin. Another aspect of the invention is where the cyclosporin is cyclosporin A.

Another aspect of the invention is a composition where the compound having anti-HCV activity is selected from the group consisting of interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

Another aspect of the invention is a composition where the compound having anti-HCV activity is effective to inhibit the function of a target selected from HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

Another aspect of the invention is a composition comprising a compound, or a pharmaceutically acceptable salt thereof, a pharmaceutically acceptable carrier, an interferon and ribavirin.

Another aspect of the invention is a method of inhibiting the function of the HCV replicon comprising contacting the HCV replicon with a compound or a pharmaceutically acceptable salt thereof.

Another aspect of the invention is a method of inhibiting the function of the HCV NS5B protein comprising contacting the HCV NS5B protein with a compound or a pharmaceutically acceptable salt thereof.

Another aspect of the invention is a method of treating an HCV infection in a patient comprising administering to the patient a therapeutically effective amount of a compound or a pharmaceutically acceptable salt thereof. In another embodiment the compound is effective to inhibit the function of the HCV replicon. In another embodiment the compound is effective to inhibit the function of the HCV NS5B protein.

Another aspect of the invention is a method of treating an HCV infection in a patient comprising administering to the patient a therapeutically effective amount of a compound, or a pharmaceutically acceptable salt thereof, in conjunction with (prior to, after, or concurrently) another compound having anti-HCV activity.

Another aspect of the invention is the method where the other compound having anti-HCV activity is an interferon or a ribavirin.

Another aspect of the invention is the method where the interferon is selected from interferon alpha 2B, pegylated interferon alpha, consensus interferon, interferon alpha 2A, interferon lambda, and lymphoblastoid interferon tau.

Another aspect of the invention is the method where the other compound having anti-HCV activity is a cyclosporin.

Another aspect of the invention is the method where the cyclosporin is cyclosporin A.

Another aspect of the invention is the method where the other compound having anti-HCV activity is selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

Another aspect of the invention is the method where the other compound having anti-HCV activity is effective to inhibit the function of a target selected from the group consisting of HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

Another aspect of the invention is the method where the other compound having anti-HCV activity is effective to inhibit the function of target in the HCV life cycle other than the HCV NS5B protein.

"Therapeutically effective" means the amount of agent required to provide a meaningful patient benefit as understood by practitioners in the field of hepatitis and HCV infection.

"Patient" means a person infected with the HCV virus and suitable for therapy as understood by practitioners in the field of hepatitis and HCV infection.

"Treatment," "therapy," "regimen," "HCV infection," and related terms are used as understood by practitioners in the field of hepatitis and HCV infection.

The compounds of this invention are generally given as pharmaceutical compositions comprised of a therapeutically effective amount of a compound or its pharmaceutically acceptable salt and a pharmaceutically acceptable carrier and may contain conventional excipients. Pharmaceutically acceptable carriers are those conventionally known carriers having acceptable safety profiles. Compositions encompass all common solid and liquid forms including for example capsules, tablets, lozenges, and powders as well as liquid suspensions, syrups, elixirs, and solutions. Compositions are made using common formulation techniques, and conventional excipients (such as binding and wetting agents) and vehicles (such as water and alcohols) are generally used for compositions. See, for example, *Remington's Pharmaceutical Sciences*, Mack Publishing Company, Easton, Pa., 17th edition, 1985.

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other agents will be present in a unit range similar to agents of that class used clinically. Typically, this is 0.25-1000 mg/unit.

Liquid compositions are usually in dosage unit ranges. Generally, the liquid composition will be in a unit dosage range of about 1-100 mg/mL. Some examples of dosages are 1 mg/mL, 10 mg/mL, 25 mg/mL, 50 mg/mL, and 100 mg/mL. Generally, other agents will be present in a unit range similar to agents of that class used clinically. Typically, this is about 1-100 mg/mL.

The invention encompasses all conventional modes of administration; oral and parenteral methods are preferred. Generally, the dosing regimen will be similar to other agents used clinically. Typically, the daily dose will be about 1-100 mg/kg body weight daily. Generally, more compound is required orally and less parenterally. The specific dosing regimen, however, will be determined by a physician using sound medical judgment.

The invention also encompasses methods where the compound is given in combination therapy. That is, the compound can be used in conjunction with, but separately from, other agents useful in treating hepatitis and HCV infection. In these combination methods, the compound will generally be given in a daily dose of about 1-100 mg/kg body weight daily in conjunction with other agents. The other agents generally will be given in the amounts used therapeutically. The specific dosing regimen, however, will be determined by a physician using sound medical judgment.

Some examples of compounds suitable for compositions and methods are listed in Table 1.

TABLE 1

| Brand Name | Physiological Class | Type of Inhibitor or Target | Source Company |
| --- | --- | --- | --- |
| NIM811 | | Cyclophilin Inhibitor | Novartis |
| Zadaxin | | Immuno-modulator | Sciclone |
| Suvus | | Methylene blue | Bioenvision |
| Actilon (CPG10101) | | TLR9 agonist | Coley |
| Batabulin (T67) | Anticancer | β-tubulin inhibitor | Tularik Inc., South San Francisco, CA |
| ISIS 14803 | Antiviral | antisense | ISIS Pharmaceuticals Inc, Carlsbad, CA/Elan Phamaceuticals Inc., New York, NY |
| Summetrel | Antiviral | antiviral | Endo Pharmaceuticals Holdings Inc., Chadds Ford, PA |
| GS-9132 (ACH-806) | Antiviral | HCV Inhibitor | Achillion/Gilead |
| Pyrazolopyrimidine compounds and salts From WO-2005047288 26 May 2005 | Antiviral | HCV Inhibitors | Arrow Therapeutics Ltd. |
| Levovirin | Antiviral | IMPDH inhibitor | Ribapharm Inc., Costa Mesa, CA |
| Merimepodib (VX-497) | Antiviral | IMPDH inhibitor | Vertex Pharmaceuticals Inc., Cambridge, MA |
| XTL-6865 (XTL-002) | Antiviral | monoclonal antibody | XTL Biopharmaceuticals Ltd., Rehovot, Isreal |
| Telaprevir (VX-950, LY-570310) | Antiviral | NS3 serine protease inhibitor | Vertex Pharmaceuticals Inc., Cambridge, MA/Eli Lilly and Co. Inc., Indianapolis, IN |
| HCV-796 | Antiviral | NS5B Replicase Inhibitor | Wyeth/Viropharma |
| NM-283 | Antiviral | NS5B Replicase Inhibitor | Idenix/Novartis |
| GL-59728 | Antiviral | NS5B Replicase Inhibitor | Gene Labs/Novartis |
| GL-60667 | Antiviral | NS5B Replicase Inhibitor | Gene Labs/Novartis |
| 2'C MeA | Antiviral | NS5B Replicase Inhibitor | Gilead |

TABLE 1-continued

| Brand Name | Physiological Class | Type of Inhibitor or Target | Source Company |
|---|---|---|---|
| PSI 6130 | Antiviral | NS5B Replicase Inhibitor | Roche |
| R1626 | Antiviral | NS5B Replicase Inhibitor | Roche |
| 2'C Methyl adenosine | Antiviral | NS5B Replicase Inhibitor | Merck |
| JTK-003 | Antiviral | RdRp inhibitor | Japan Tobacco Inc., Tokyo, Japan |
| Levovirin | Antiviral | ribavirin | ICN Pharmaceuticals, Costa Mesa, CA |
| Ribavirin | Antiviral | ribavirin | Schering-Plough Corporation, Kenilworth, NJ |
| Viramidine | Antiviral | Ribavirin Prodrug | Ribapharm Inc., Costa Mesa, CA |
| Heptazyme | Antiviral | ribozyme | Ribozyme Pharmaceuticals Inc., Boulder, CO |
| BILN-2061 | Antiviral | serine protease inhibitor | Boehringer Ingelheim Pharma KG, Ingelheim, Germany |
| SCH 503034 | Antiviral | serine protease inhibitor | Schering Plough |
| Zadazim | Immune modulator | Immune modulator | SciClone Pharmaceuticals Inc., San Mateo, CA |
| Ceplene | Immunomodulator | immune modulator | Maxim Pharmaceuticals Inc., San Diego, CA |
| CellCept | Immunosuppressant | HCV IgG immuno-suppressant | F. Hoffmann-La Roche LTD, Basel, Switzerland |
| Civacir | Immunosuppressant | HCV IgG immuno-suppressant | Nabi Biopharmaceuticals Inc., Boca Raton, FL |
| Albuferon-α | Interferon | albumin IFN-α2b | Human Genome Sciences Inc., Rockville, MD |
| Infergen A | Interferon | IFN alfacon-1 | InterMune Pharmaceuticals Inc., Brisbane, CA |
| Omega IFN | Interferon | IFN-ω | Intarcia Therapeutics |
| IFN-β and EMZ701 | Interferon | IFN-β and EMZ701 | Transition Therapeutics Inc., Ontario, Canada |
| Rebif | Interferon | IFN-β1a | Serono, Geneva, Switzerland |
| Roferon A | Interferon | IFN-α2a | F. Hoffmann-La Roche LTD, Basel, Switzerland |
| Intron A | Interferon | IFN-α2b | Schering-Plough Corporation, Kenilworth, NJ |
| Intron A and Zadaxin | Interferon | IFN-α2b/α1-thymosin | RegeneRx Biopharma. Inc., Bethesda, MD/ SciClone Pharmaceuticals Inc, San Mateo, CA |
| Rebetron | Interferon | IFN-α2b/ribavirin | Schering-Plough Corporation, Kenilworth, NJ |
| Actimmune | Interferon | INF-γ | InterMune Inc., Brisbane, CA |
| Interferon-β | Interferon | Interferon-β-1a | Serono |
| Multiferon | Interferon | Long lasting IFN | Viragen/ Valentis |
| Wellferon | Interferon | Lympho-blastoid IFN-αn1 | GlaxoSmithKline plc, Uxbridge, UK |
| Omniferon | Interferon | natural IFN-α | Viragen Inc., Plantation, FL |
| Pegasys | Interferon | PEGylated IFN-α2a | F. Hoffmann-La Roche LTD, Basel, Switzerland |

TABLE 1-continued

| Brand Name | Physiological Class | Type of Inhibitor or Target | Source Company |
|---|---|---|---|
| Pegasys and Ceplene | Interferon | PEGylated IFN-α2a/immune modulator | Maxim Pharmaceuticals Inc., San Diego, CA |
| Pegasys and Ribavirin | Interferon | PEGylated IFN-α2a/ribavirin | F. Hoffmann-La Roche LTD, Basel, Switzerland |
| PEG-Intron | Interferon | PEGylated IFN-α2b | Schering-Plough Corporation, Kenilworth, NJ |
| PEG-Intron/Ribavirin | Interferon | PEGylated IFN-α2b/ribavirin | Schering-Plough Corporation, Kenilworth, NJ |
| IP-501 | Liver protection | antifibrotic | Indevus Pharmaceuticals Inc., Lexington, MA |
| IDN-6556 | Liver protection | caspase inhibitor | Idun Pharmaceuticals Inc., San Diego, CA |
| ITMN-191 (R-7227) | Antiviral | serine protease inhibitor | InterMune Pharmaceuticals Inc., Brisbane, CA |
| GL-59728 | Antiviral | NS5B Replicase Inhibitor | Genelabs |
| ANA-971 | Antiviral | TLR-7 agonist | Anadys |
| Boceprevir | Antiviral | serine protease inhibitor | Schering Plough |
| TMS-435 | Antiviral | serine protease inhibitor | Tibotec BVBA, Mechelen, Belgium |
| BI-201335 | Antiviral | serine protease inhibitor | Boehringer Ingelheim Pharma KG, Ingelheim, Germany |
| MK-7009 | Antiviral | serine protease inhibitor | Merck |
| PF-00868554 | Antiviral | replicase inhibitor | Pfizer |
| ANA598 | Antiviral | Non-Nucleoside NS5B Polymerase Inhibitor | Anadys Pharmaceuticals, Inc., San Diego, CA, USA |
| IDX375 | Antiviral | Non-Nucleoside Replicase Inhibitor | Idenix Pharmaceuticals, Cambridge, MA, USA |
| BILB 1941 | Antiviral | NS5B Polymerase Inhibitor | Boehringer Ingelheim Canada Ltd R&D, Laval, QC, Canada |
| PSI-7851 | Antiviral | Nucleoside Polymerase Inhibitor | Pharmasset, Princeton, NJ, USA |
| PSI-7977 | Antiviral | Nucleotide NS5B Polymerase Inhibitor | Pharmasset, Princeton, NJ, USA |
| VCH-759 | Antiviral | NS5B Polymerase Inhibitor | ViroChem Pharma |
| VCH-916 | Antiviral | NS5B Polymerase Inhibitor | ViroChem Pharma |
| GS-9190 | Antiviral | NS5B Polymerase Inhibitor | Gilead |
| Peg-interferon lamda | Antiviral | Interferon | ZymoGenetics/Bristol-Myers Squibb |

Synthetic Methods

The compounds may be made by methods available in the art, as well as those described below and including variations within the skill of the art. Some reagents and intermediates are known in the art. Other reagents and intermediates can be made by methods known in the art using readily available materials. The variables (e.g. numbered "R" substituents) used to describe the synthesis of the compounds are intended only to illustrate how to make the compounds and are not to be confused with variables used in the claims or in other sections of the specification. The following methods are for illustrative purposes and are not intended to limit the scope of the invention.

Abbreviations used in the schemes generally follow conventions used in the art. Chemical abbreviations used in the specification and examples are defined as follows: "NaHMDS" for sodium bis(trimethylsilyl)amide; "DMF" for N,N-dimethylformamide; "MeOH" for methanol; "NBS" for N-bromosuccinimide; "Ar" for aryl; "TFA" for trifluoroacetic acid; "LAH" for lithium aluminum hydride; "BOC", "DMSO" for dimethylsulfoxide; "h" for hours; "rt" for room temperature or retention time (context will dictate); "min" for minutes; "EtOAc" for ethyl acetate; "THF" for tetrahydrofuran; "EDTA" for ethylenediaminetetraacetic acid; "Et$_2$O" for diethyl ether; "DMAP" for 4-dimethylaminopyridine; "DCE" for 1,2-dichloroethane; "ACN" for acetonitrile; "DME" for 1,2-dimethoxyethane; "HOBt" for 1-hydroxybenzotriazole hydrate; "DIEA" for diisopropylethylamine, "Nf" for CF$_3$(CF$_2$)$_3$SO$_2$—; and "TMOF" for trimethylorthoformate.

Abbreviations are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "sat'd" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Chemistry Experimental

LC/MS Method (i.e., Compound Identification)

All Liquid Chromatography (LC) data were recorded on a Shimadzu LC-10AS or LC-20AS liquid chromotograph using a SPD-10AV or SPD-20A UV-Vis detector and Mass Spectrometry (MS) data were determined with a Micromass Platform for LC in electrospray mode.

HPLC Method (i.e., Compound Isolation)

Compounds purified by preparative HPLC were diluted in methanol (1.2 mL) and purified using a Shimadzu LC-8A or LC-10A automated preparative HPLC system.

Syntheses of Intermediates:

Preparation of 4-(4-(1-(4-chlorophenyl)cyclopropylamino)-6-(2,2,2-trifluoroethoxy)-1,3,5-triazin-2-ylamino)benzoic acid

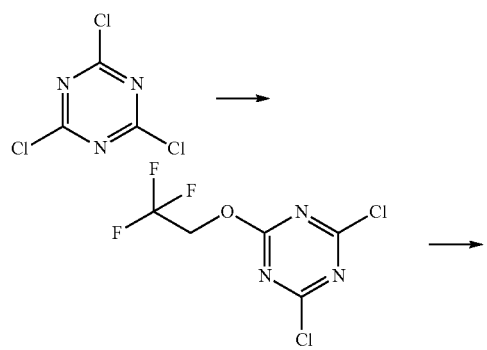

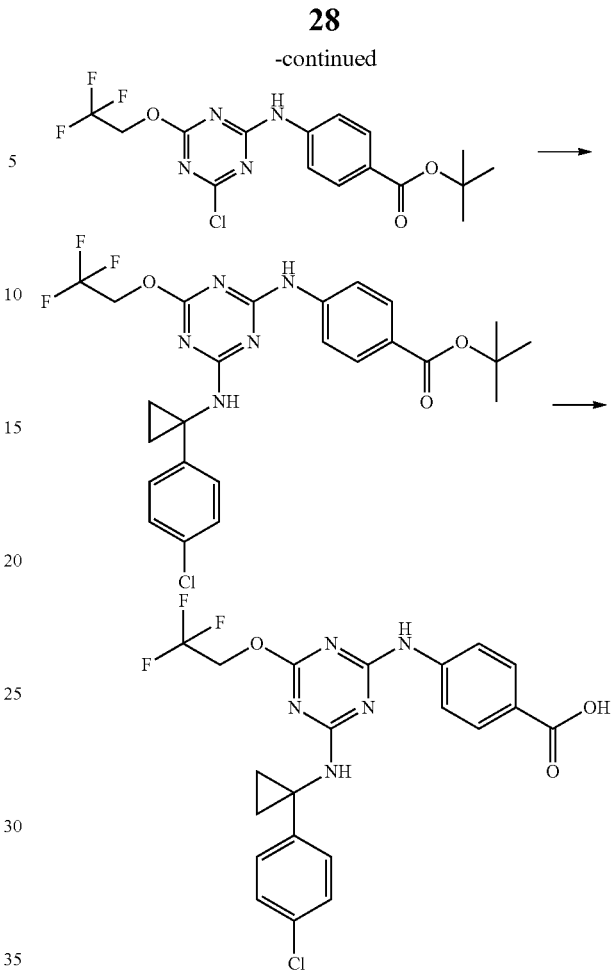

Step 1: To a solution of 2,4,6-trichloro-1,3,5-triazine (15 g) in THF (300 mL) was added 2,2,2-trifluoroethanol (8.14 g) and Hunig'sBase (15.63 mL). The resulting mixture was stirred for 16 hours. After removal of most THF and precipitate through a plug washing with THF, the filtrate was concentrate to give a crude that will be used as it is.

Step 2: To a solution of the product in Step 1 above (10 g) in THF (100 mL) was added tert-butyl 4-aminobenzoate (7.79 g) and Hunig'sBase (7.04 mL). The resulting mixture was stirred for 16 h. The precipitate was filtered and washed with Et$_2$O, dried, then washed with water and dried to give 10.6 g of tert-butyl 4-(4-chloro-6-(2,2,2-trifluoroethoxy)-1,3,5-triazin-2-ylamino)benzoate as a solid.

| tert-butyl 4-(4-chloro-6-(2,2,2-trifluoroethoxy)-1,3,5-triazin-2-ylamino)benzoate | |
|---|---|
| MS (M + H)$^+$ Calcd. | 405.1 |
| MS (M + H)$^+$ Observ. | 405.0 |
| LC Condition | |
| Solvent A | 100% Water-0.1% TFA |
| Solvent B | 100% ACN-0.1% TFA |
| Start % B | 2 |
| Final % B | 98 |
| Gradient Time | 1.6 min |
| Stop Time | 1.8 min |
| Flow Rate | 0.8 mL/min |
| Wavelength | 220 |
| Solvent Pair | ACN-H$_2$0-0.1% TFA |
| Column | Aquity UPLC BEH C18 1.7 um |

Step 3: To a slurry of tert-butyl 4-(4-chloro-6-(2,2,2-trifluoroethoxy)-1,3,5-triazin-2-ylamino)benzoate (3.6 g) and 1-(4-chlorophenyl)cyclopropanamine (1.49 g) in THF (50 mL) was stirred for 5 hours at 80° C. The precipitate was filtrated through a plug washing with THF to give a crude product that was purified by Biotage eluting with 4/1-hexane/ethyl acetate to give 1.8 g of tert-butyl 4-(4-(1-(4-chlorophenyl)cyclopropylamino)-6-(2,2,2-trifluoroethoxy)-1,3,5-triazin-2-ylamino)benzoate as a solid.

| tert-butyl 4-(4-(1-(4-chlorophenyl)cyclopropylamino)-6-(2,2,2-trifluoroethoxy)-1,3,5-triazin-2-ylamino)benzoate | |
| --- | --- |
| MS (M + H)$^+$ Calcd. | 536.2 |
| MS (M + H)$^+$ Observ. | 536.0 |
| LC Condition | |
| Solvent A | 100% Water-0.1% TFA |
| Solvent B | 100% ACN-0.1% TFA |
| Start % B | 2 |
| Final % B | 98 |
| Gradient Time | 1.6 min |
| Stop Time | 1.8 min |
| Flow Rate | 0.8 mL/min |
| Wavelength | 220 |
| Solvent Pair | ACN-H$_2$0-0.1% TFA |
| Column | Aquity UPLC BEH C18 1.7 um |

Step 4: A solution of above tert-butyl 4-(4-(1-(4-chlorophenyl)cyclopropylamino)-6-(2,2,2-trifluoroethoxy)-1,3,5-triazin-2-ylamino)benzoate (4 g) and HCl in dioxane (7.46 ml, 4M) was stirred for 4 hours. Concentration gave 3.58 g of 4-(4-(1-(4-chlorophenyl)cyclopropylamino)-6-(2,2,2-trifluoroethoxy)-1,3,5-triazin-2-ylamino)benzoic acid as a solid.

| 4-(4-(1-(4-chlorophenyl)cyclopropylamino)-6-(2,2,2-trifluoroethoxy)-1,3,5-triazin-2-ylamino)benzoic acid | |
| --- | --- |
| MS (M + H)$^+$ Calcd. | 480.1 |
| MS (M + H)$^+$ Observ. | 480.1 |
| LC Condition | |
| Solvent A | 100% Water-0.1% TFA |
| Solvent B | 100% ACN-0.1% TFA |
| Start % B | 2 |
| Final % B | 98 |
| Gradient Time | 1.6 min |
| Stop Time | 1.8 min |
| Flow Rate | 0.8 mL/min |
| Wavelength | 220 |
| Solvent Pair | ACN-H$_2$0-0.1% TFA |
| Column | Aquity UPLC BEH C18 1.7 um |

Preparation of (S)-methyl 3-(tert-butoxycarbonylamino)-2-(4-(4-(1-(4-chlorophenyl)cyclopropylamino)-6-(2,2,2-trifluoroethoxy)-1,3,5-triazin-2-ylamino)benzamido)propanoate

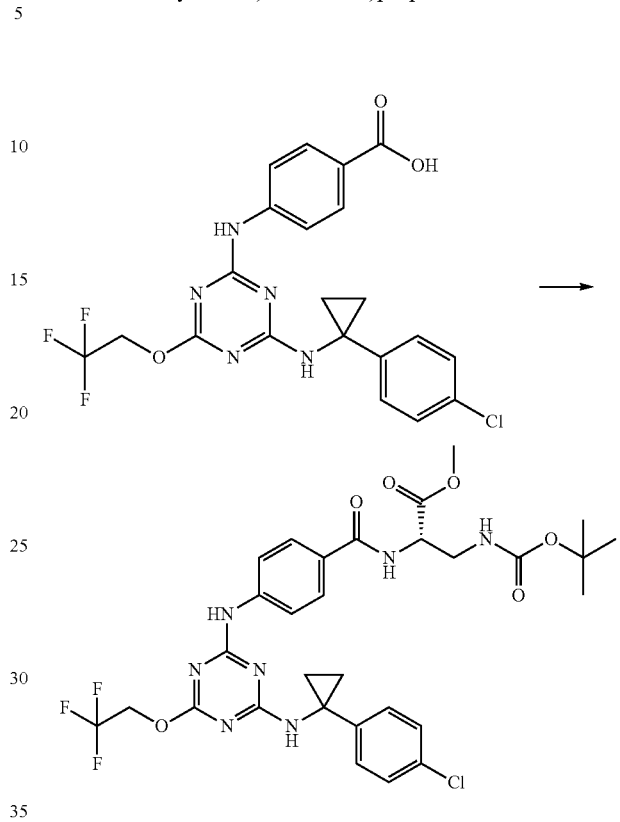

To a solution of 4-(4-(1-(4-chlorophenyl)cyclopropylamino)-6-(2,2,2-trifluoroethoxy)-1,3,5-triazin-2-ylamino)benzoic acid (50 mg) in DMF (2 mL) was added O-(benzotriazol-1-yl-N,N,N',N'-tetramethyluronium tetrafluoroborate (23.82 mg) and (S)-methyl 2-amino-3-(tert-butoxycarbonylamino)propanoate hydrochloride (18.90 mg) and iPr$_2$NEt (0.052 ml). After stirring at rt for 4 h, the mixture was purified by preparative HPLC to give (S)-methyl 3-(tert-butoxycarbonylamino)-2-(4-(4-(1-(4-chlorophenyl)cyclopropylamino)-6-(2,2,2-trifluoroethoxy)-1,3,5-triazin-2-ylamino)benzamido)propanoate.

| (S)-methyl 3-(tert-butoxycarbonylamino)-2-(4-(4-(1-(4-chlorophenyl)cyclopropylamino)-6-(2,2,2-trifluoroethoxy)-1,3,5-triazin-2-ylamino)benzamido)propanoate | |
| --- | --- |
| MS (M + H)$^+$ Calcd. | 680.2 |
| MS (M + H)$^+$ Observ. | 680.3 |
| Retention Time | 3.44 min |
| LC Condition | |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 4 min |
| Flow Rate | 0.8 mL/min |
| Wavelength | 220 |
| Solvent Pair | ACN:Water:Ammonium Actetate |
| Column | Phenomenex Luna C18, 50 × 2, 3u |

Preparation of (S)-methyl 3-amino-2-(4-(4-(1-(4-chlorophenyl)cyclopropylamino)-6-(2,2,2-trifluoroethoxy)-1,3,5-triazin-2-ylamino)benzamido)propanoate

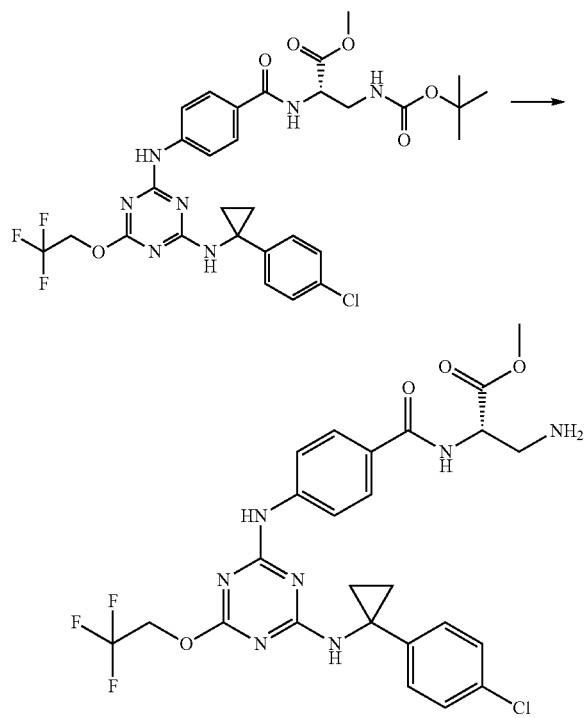

To a solution of (S)-methyl 3-(tert-butoxycarbonylamino)-2-(4-(4-(1-(4-chlorophenyl)cyclopropylamino)-6-(2,2,2-trifluoroethoxy)-1,3,5-triazin-2-ylamino)benzamido)propanoate (1 g) in CH₂Cl₂ (10 mL) was added TFA (3 mL). The mixture was stirred at room temperature for 16 hours. All the solvents were removed under vacuum to give (S)-methyl 3-amino-2-(4-(4-(1-(4-chlorophenyl)cyclopropylamino)-6-(2,2,2-trifluoroethoxy)-1,3,5-triazin-2-ylamino)benzamido)propanoate (0.8 g).

| (S)-methyl 3-amino-2-(4-(4-(1-(4-chlorophenyl)cyclopropylamino)-6-(2,2,2-trifluoroethoxy)-1,3,5-triazin-2-ylamino)benzamido)propanoate | |
|---|---|
| MS (M + H)⁺ Calcd. | 580.2 |
| MS (M + H)⁺ Observ. | 580.0 |
| Retention Time | 1.35 min |
| LC Condition | |
| Solvent A | 90% Water-10% Methanol-0.1% TFA |
| Solvent B | 10% Water-90% Methanol-0.1% TFA |
| Start % B | 50 |
| Final % B | 100 |
| Gradient Time | 2 min |
| Flow Rate | 1 mL/min |
| Wavelength | 220 |
| Solvent Pair | Water-Methanol-TFA |
| Column | PHENOMENEX-LUNA 2.0 × 30 mm 3 um |

Syntheses of Claim I:

Synthesis of Compound 1001, (S)-methyl 2-(4-(4-(1-(4-chlorophenyl)cyclopropylamino)-6-(2,2,2-trifluoroethoxy)-1,3,5-triazin-2-ylamino)benzamido)-3-(2-methoxy-3,4-dioxocyclobut-1-enylamino)propanoate A mixture of (S)-methyl 3-amino-2-(4-(4-(1-(4-chlorophenyl)cyclopropylamino)-6-(2,2,2-trifluoroethoxy)-1,3,5-triazin-2-ylamino)benzamido)propanoate (20 mg) and 3,4-diethoxycyclobut-3-ene-1,2-dione (7.35 mg) in methanol (2 mL) was heated at 100° C. for 16 hours. After cooling to room temperature, the mixture was purified by preparative HPLC to give (S)-methyl 2-(4-(4-(1-(4-chlorophenyl)cyclopropylamino)-6-(2,2,2-trifluoroethoxy)-1,3,5-triazin-2-ylamino)benzamido)-3-(2-methoxy-3,4-dioxocyclobut-1-enylamino)propanoate (4 mg).

| Compound 1001 | |
|---|---|
| MS (M + H)⁺ Calcd. | 690.2 |
| MS (M + H)⁺ Observ. | 690.1 |
| Retention Time | 3.01 min |
| LC Condition | |
| Solvent A | 90% Water-10% Methanol-0.1% TFA |
| Solvent B | 10% Water-90% Methanol-0.1% TFA |
| Start % B | 50 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

Synthesis of Compound 1002, (S)-methyl 2-(4-(4-(1-(4-chlorophenyl)cyclopropylamino)-6-(2,2,2-trifluoroethoxy)-1,3,5-triazin-2-ylamino)benzamido)-3-(2-ethoxy-3,4-dioxocyclobut-1-enylamino)propanoate and Compound 1003, (S)-methyl 2-(4-(4-(1-(4-chlorophenyl)cyclopropylamino)-6-(2,2,2-trifluoroethoxy)-1,3,5-triazin-2-ylamino)benzamido)-3-(2-hydroxy-3,4-dioxocyclobut-1-enylamino)propanoate

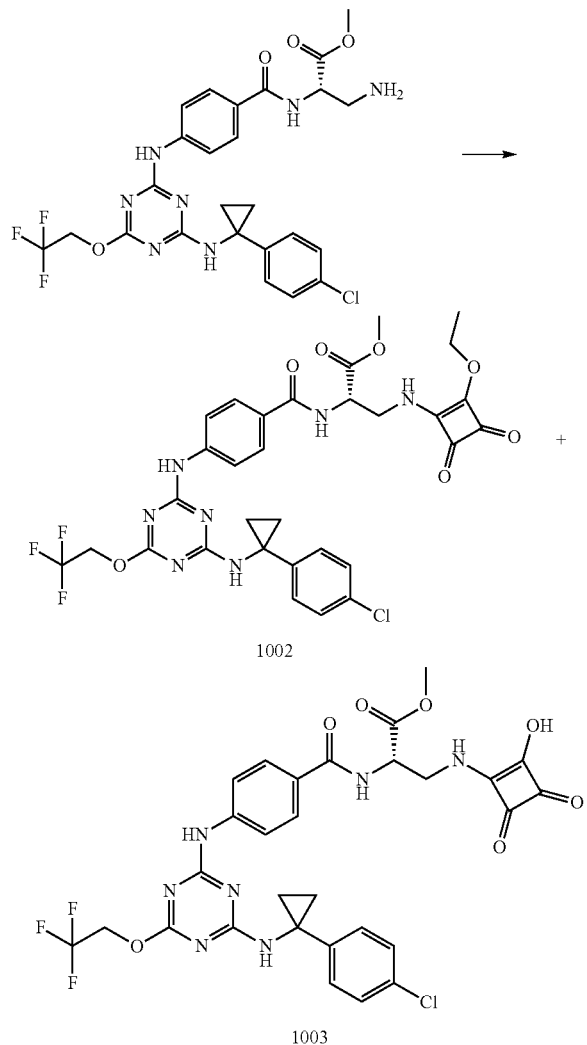

| Compound 1002 | |
|---|---|
| MS (M + H)+ Calcd. | 704.2 |
| MS (M + H)+ Observ. | 704.1 |
| Retention Time | 3.15 min |
| LC Condition | |
| Solvent A | 90% Water-10% Methanol-0.1% TFA |
| Solvent B | 10% Water-90% Methanol-0.1% TFA |
| Start % B | 50 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

| Compound 1003 | |
|---|---|
| MS (M + H)+ Calcd. | 676.2 |
| MS (M + H)+ Observ. | 676.1 |
| Retention Time | 2.90 min |
| LC Condition | |
| Solvent A | 90% Water-10% Methanol-0.1% TFA |
| Solvent B | 10% Water-90% Methanol-0.1% TFA |
| Start % B | 50 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

Synthesis of Compound 1004, (S)-2-(4-(4-(1-(4-chlorophenyl)cyclopropylamino)-6-(2,2,2-trifluoroethoxy)-1,3,5-triazin-2-ylamino)benzamido)-3-(2-ethoxy-3,4-dioxocyclobut-1-enylamino)propanoic acid A mixture of (S)-methyl 3-amino-2-(4-(4-(1-(4-chlorophenyl)cyclopropylamino)-6-(2,2,2-trifluoroethoxy)-1,3,5-triazin-2-ylamino)benzamido)propanoate (50 mg) and 3,4-diethoxycyclobut-3-ene-1,2-dione (22.01 mg) in ethanol (2 mL) was heated at 100° C. for 16 hours. After cooling to room temperature, the mixture was purified by preparative HPLC to give (S)-methyl 2-(4-(4-(1-(4-chlorophenyl)cyclopropylamino)-6-(2,2,2-trifluoroethoxy)-1,3,5-triazin-2-ylamino)benzamido)-3-(2-hydroxy-3,4-dioxocyclobut-1-enylamino)propanoate (8 mg) and (S)-methyl 2-(4-(4-(1-(4-chlorophenyl)cyclopropylamino)-6-(2,2,2-trifluoroethoxy)-1,3,5-triazin-2-ylamino)benzamido)-3-(2-ethoxy-3,4-dioxocyclobut-1-enylamino)propanoate (12 mg).

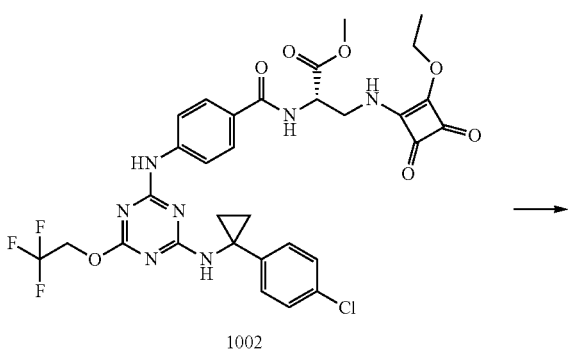

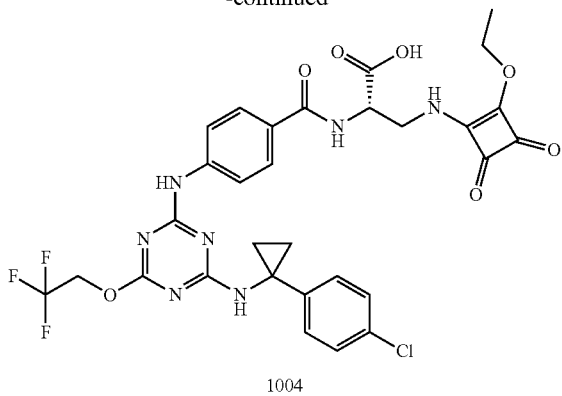

1004

A mixture of (S)-methyl 2-(4-(4-(1-(4-chlorophenyl)cyclopropylamino)-6-(2,2,2-trifluoroethoxy)-1,3,5-triazin-2-ylamino)benzamido)-3-(2-ethoxy-3,4-dioxocyclobut-1-enylamino)propanoate (10 mg) and K$_2$CO$_3$ (7.85 mg, 0.057 mmol) in acetone-water (2 mL, 1:1 by volume) was heated at 100° C. for 3 hours. All the solvents were removed under vacuum and the residue was purified by preparative HPLC to give (S)-2-(4-(4-(1-(4-chlorophenyl)cyclopropylamino)-6-(2,2,2-trifluoroethoxy)-1,3,5-triazin-2-ylamino)benzamido)-3-(2-ethoxy-3,4-dioxocyclobut-1-enylamino)propanoic acid (3.8 mg).

| Compound 1004 | |
|---|---|
| MS (M + H)$^+$ Calcd. | 690.2 |
| MS (M + H)$^+$ Observ. | 690.1 |
| Retention Time | 3.60 min |
| LC Condition | |
| Solvent A | 90% Water-10% Methanol-0.1% TFA |
| Solvent B | 10% Water-90% Methanol-0.1% TFA |
| Start % B | 30 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

Synthesis of Compound 1005, 4-((4-((1-(4-chlorophenyl)cyclopropyl)amino)-6-(2,2,2-trifluoroethoxy)-1,3,5-triazin-2-yl)amino)-N-(3-((2-ethoxy-3,4-dioxocyclobut-1-en-1-yl)amino)-2,2-dimethylpropyl)benzamide

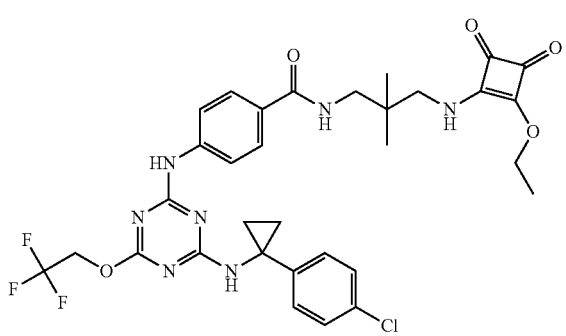 [SMILES: CCOc1c(NCC(C)(C)CNC(=O)c2ccc(Nc3nc(NC4(c5ccc(Cl)cc5)CC4)nc(OCC(F)(F)F)n3)cc2)c(=O)c1=O]

Compound 1005 was made using the same procedure preparing Compound 1002, using N-(3-amino-2,2-dimethylpropyl)-4-((4-((1-(4-chlorophenyl)cyclopropyl)amino)-6-(2,2,2-trifluoroethoxy)-1,3,5-triazin-2-yl)amino)benzamide as the starting material.

| Compound 1005 | |
|---|---|
| MS (M + H)$^+$ Calcd. | 688.2 |
| MS (M + H)$^+$ Observ. | 688.4 |
| Retention Time | 1.87 min |
| LC Condition | |
| Solvent A | 5% ACN:95% Water:10 mM Ammonium Actetate |
| Solvent B | 95% ACN:5% Water:10 mM Ammonium Actetate |
| Start % B | 30 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex LUNA C18, 30 × 2, 3u |

Synthesis of Compound 1006, 4-((4(1-(4-chlorophenyl)cyclopropyl)amino)-6-(2,2,2-trifluoroethoxy)-1,3,5-triazin-2-yl)amino)-N-(3-((2-hydroxy-3,4-dioxocyclobut-1-en-1-yl)amino)-2,2-dimethylpropyl)benzamide

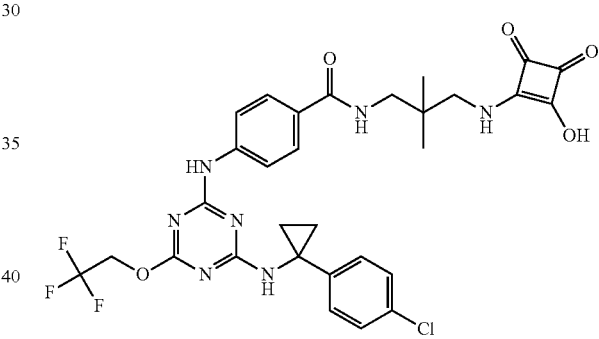

K$_2$CO$_3$ (5.2 mg) was added into the solution of Compound 1005 (25 mg) in EtOH (2 mL) and water (2 mL). The reaction was carried out at room temperature for 16 hours. All the solvents were removed under vacuum and the residue was purified by preparative HPLC to give Compound 1006.

| Compound 1006 | |
|---|---|
| MS (M + H)$^+$ Calcd. | 660.2 |
| MS (M + H)$^+$ Observ. | 660.2 |
| Retention Time | 2.28 min |
| LC Condition | |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 2 min |
| Flow Rate | 1 mL/min |
| Wavelength | 220 |
| Solvent Pair | Water-Methanol-TFA |
| Column | PHENOMENEX-LUNA 2.0 × 30 mm 3 um |

General Procedure to Prepare Claim I from Compound 1005:

iPr$_2$NEt oe Et$_3$N (1-20 eq.) and amine was added into a solution of Compound 1005 were combined in MeOH, EtOH, THF or DMF. The mixture was stirred at room temperature or 115° C. for 17 hours. The solvents were removed via evaporation at reduced pressure and the residue was purified by preparative HPLC system.

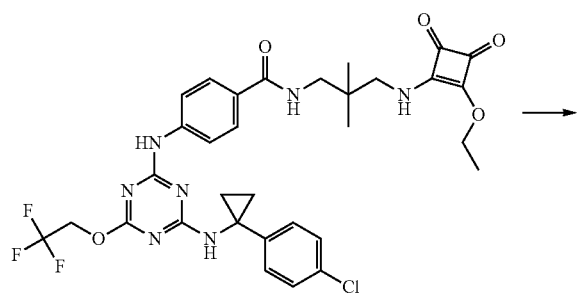

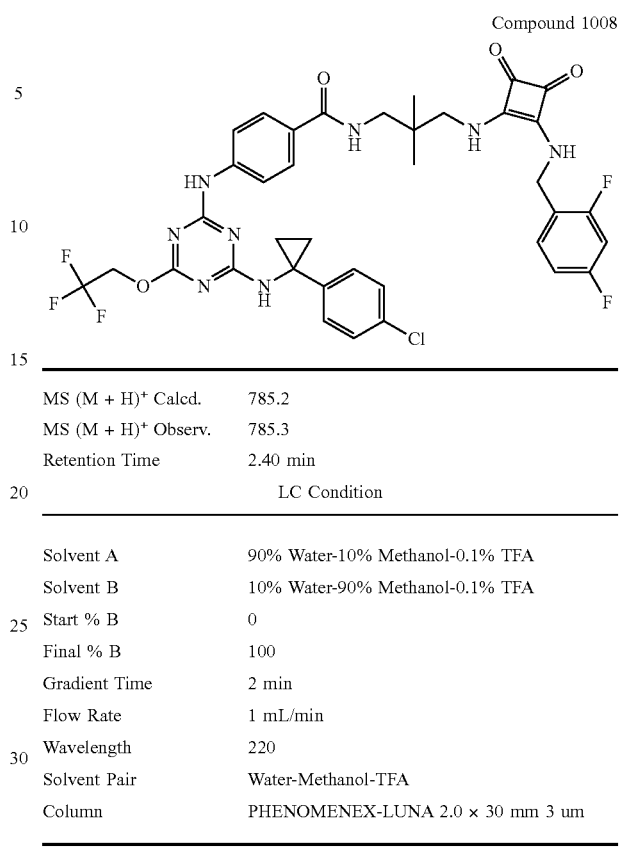

Compound 1008

| | |
|---|---|
| MS (M + H)$^+$ Calcd. | 785.2 |
| MS (M + H)$^+$ Observ. | 785.3 |
| Retention Time | 2.40 min |
| LC Condition | |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 2 min |
| Flow Rate | 1 mL/min |
| Wavelength | 220 |
| Solvent Pair | Water-Methanol-TFA |
| Column | PHENOMENEX-LUNA 2.0 × 30 mm 3 um |

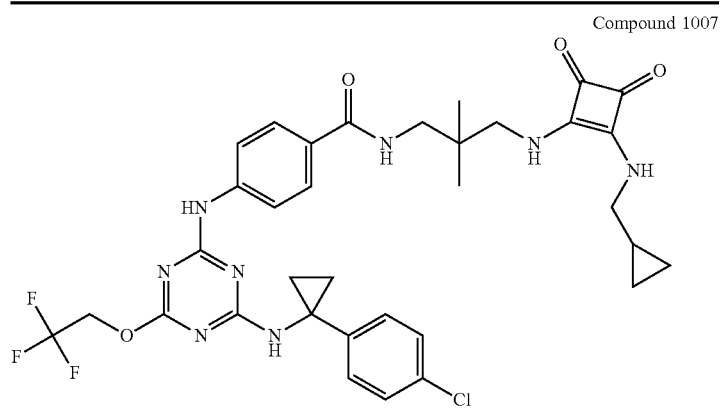

Compound 1007

| | |
|---|---|
| MS (M + H)$^+$ Calcd. | 713.2 |
| MS (M + H)$^+$ Observ. | 713.3 |
| Retention Time | 2.37 min |
| LC Condition | |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 2 min |
| Flow Rate | 1 mL/min |
| Wavelength | 220 |
| Solvent Pair | Water-Methanol-TFA |
| Column | PHENOMENEX-LUNA 2.0 × 30 mm 3 um |

Compound 1009

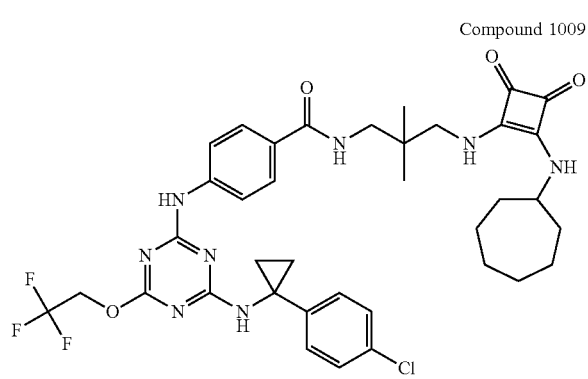

| | |
|---|---|
| MS (M + H)+ Calcd. | 755.3 |
| MS (M + H)+ Observ. | 755.3 |
| Retention Time | 2.48 min |
| LC Condition | |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 2 min |
| Flow Rate | 1 mL/min |
| Wavelength | 220 |
| Solvent Pair | Water-Methanol-TFA |
| Column | PHENOMENEX-LUNA 2.0 × 30 mm 3 um |

Compound 1010

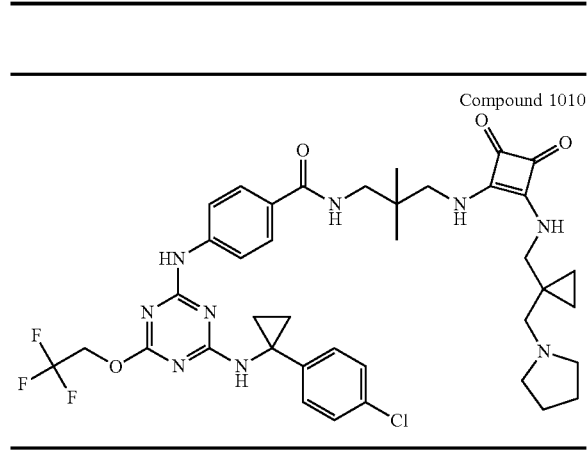

| | |
|---|---|
| MS (M + H)+ Calcd. | 796.3 |
| MS (M + H)+ Observ. | 796.5 |
| Retention Time | 2.11 min |
| LC Condition | |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 2 min |
| Flow Rate | 1 mL/min |
| Wavelength | 220 |
| Solvent Pair | Water-Methanol-TFA |
| Column | PHENOMENEX-LUNA 2.0 × 30 mm 3 um |

Compound 1013

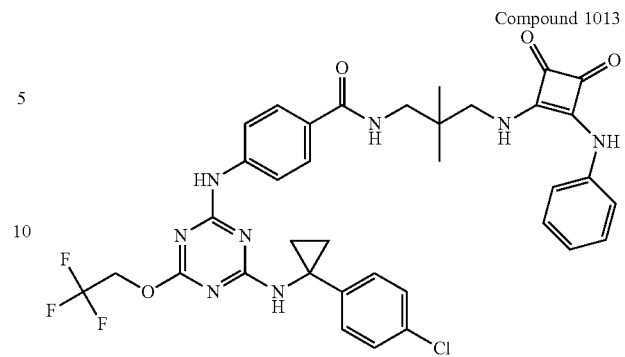

| | |
|---|---|
| MS (M + H)+ Calcd. | 735.2 |
| MS (M + H)+ Observ. | 735.3 |
| Retention Time | 2.43 min |
| LC Condition | |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 2 min |
| Flow Rate | 1 mL/min |
| Wavelength | 220 |
| Solvent Pair | Water-Methanol-TFA |
| Column | PHENOMENEX-LUNA 2.0 × 30 mm 3 um |

General procedure to prepare Claim I from (S)-methyl 4-amino-2-(4-((4-((1-(4-chlorophenyl)cyclopropyl)amino)-6-(2,2,2-trifluoroethoxy)-1,3,5-triazin-2-yl)amino)benzamido)butanoate

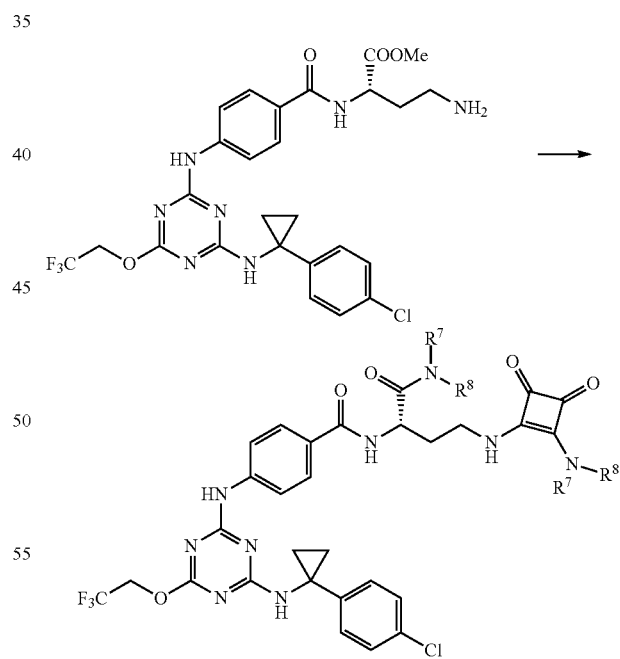

A mixture of (S)-methyl 4-amino-2-(4-((4-((1-(4-chlorophenyl)cyclopropyl)amino)-6-(2,2,2-trifluoroethoxy)-1,3,5-triazin-2-yl)amino)benzamido)butanoate (1 eq.) and 3,4-diethoxycyclobut-3-ene-1,2-dione or 3,4-dimethoxycyclobut-3-ene-1,2-dione (1-2 eq.) in ethanol was heated at 100° C. to 130° C. for 16 hours. Then, amine (10-20 eq.) and iPr₂NEt (20 eq.) were added and the resulting mixture was heated to 100° C. to 130° C. for 1-16 hours. The mixture was purified by preparative HPLC system.

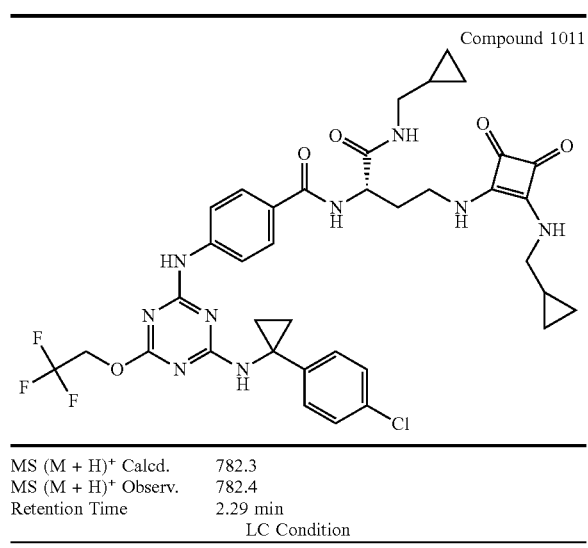

Compound 1011

| | |
|---|---|
| MS (M + H)+ Calcd. | 782.3 |
| MS (M + H)+ Observ. | 782.4 |
| Retention Time | 2.29 min |
| LC Condition | |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 2 min |
| Flow Rate | 1 mL/min |
| Wavelength | 220 |
| Solvent Pair | Water-Methanol-TFA |
| Column | PHENOMENEX-LUNA 2.0 × 30 mm 3 um |

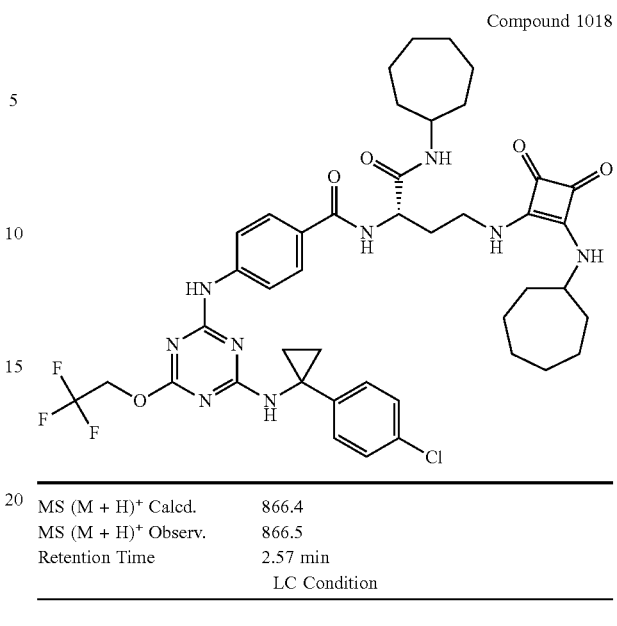

Compound 1018

| | |
|---|---|
| MS (M + H)+ Calcd. | 866.4 |
| MS (M + H)+ Observ. | 866.5 |
| Retention Time | 2.57 min |
| LC Condition | |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 2 min |
| Flow Rate | 1 mL/min |
| Wavelength | 220 |
| Solvent Pair | Water-Methanol-TFA |
| Column | PHENOMENEX-LUNA 2.0 × 30 mm 3 um |

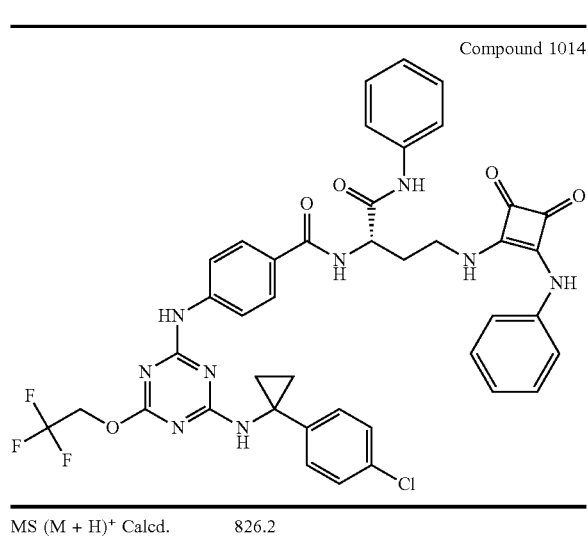

Compound 1014

| | |
|---|---|
| MS (M + H)+ Calcd. | 826.2 |
| MS (M + H)+ Observ. | 826.4 |
| Retention Time | 2.56 min |
| LC Condition | |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 2 min |
| Flow Rate | 1 mL/min |
| Wavelength | 220 |
| Solvent Pair | Water-Methanol-TFA |
| Column | PHENOMENEX-LUNA 2.0 × 30 mm 3 um |

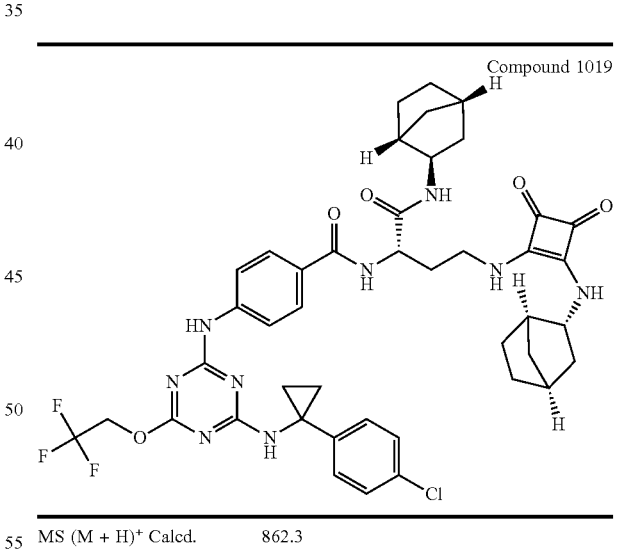

Compound 1019

| | |
|---|---|
| MS (M + H)+ Calcd. | 862.3 |
| MS (M + H)+ Observ. | 862.5 |
| Retention Time | 2.51 min |
| LC Condition | |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 2 min |
| Flow Rate | 1 mL/min |
| Wavelength | 220 |
| Solvent Pair | Water-Methanol-TFA |
| Column | PHENOMENEX-LUNA 2.0 × 30 mm 3 um |

Compound 1020

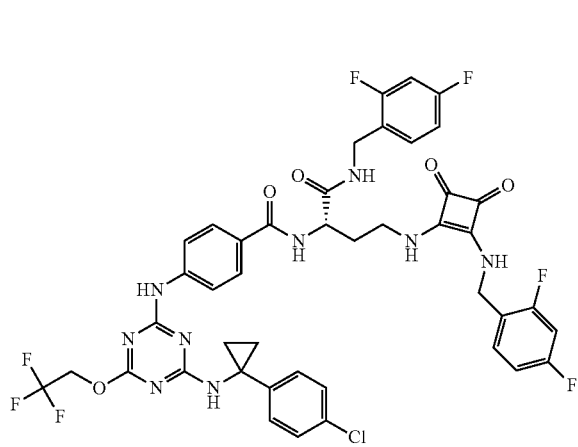 [SMILES: O=C(N[C@@H](CCNc1c(NCc2ccc(F)cc2F)c(=O)c1=O)C(=O)NCc1ccc(F)cc1F)c1ccc(Nc2nc(NC3(c4ccc(Cl)cc4)CC3)nc(OCC(F)(F)F)n2)cc1]

| | |
|---|---|
| MS (M + H)+ Calcd. | 926.2 |
| MS (M + H)+ Observ. | 926.6 |
| Retention Time | 1.91 min |

| LC Condition | |
|---|---|
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex LUNA C18, 30 × 2, 3 u |

General procedure to prepare Claim I from (S)-methyl 4-amino-2-(4-((4-((1-(4-chlorophenyl)cyclopropyl)amino)-6-(2,2,2-trifluoroethoxy)-1,3,5-triazin-2-yl)amino)benzamido)butanoate

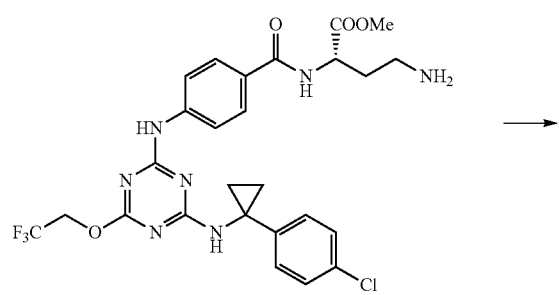

→

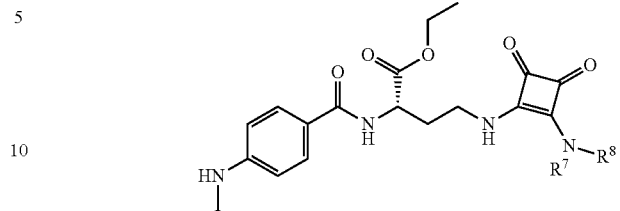

A mixture of (S)-methyl 4-amino-2-(4-((4-((1-(4-chlorophenyl)cyclopropyl)amino)-6-(2,2,2-trifluoroethoxy)-1,3,5-triazin-2-yl)amino)benzamido)butanoate (1 eq.) and 3,4-diethoxycyclobut-3-ene-1,2-dione or 3,4-dimethoxycyclobut-3-ene-1,2-dione (1-2 eq.) in ethanol was heated at 100° C. to 130° C. for 16 hours. Then, amine (10-20 eq.) and iPr$_2$NEt (20 eq.) were added and the resulting mixture was stirred at room temperature for 16-72 hours. The mixture was purified by preparative HPLC system.

Compound 1022

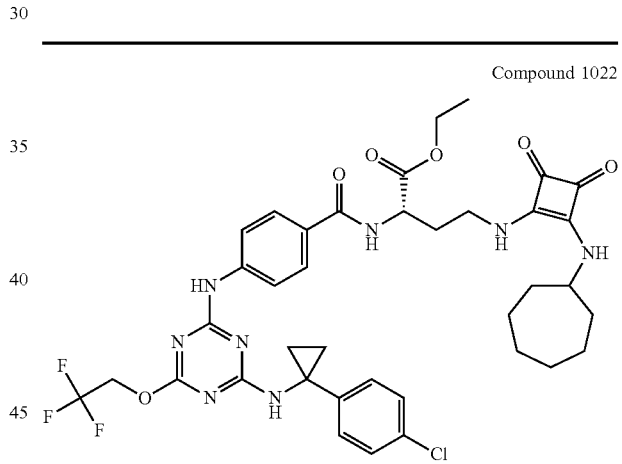

| | |
|---|---|
| MS (M + H)+ Calcd. | 799.3 |
| MS (M + H)+ Observ. | 799.4 |
| Retention Time | 2.43 min |

| LC Condition | |
|---|---|
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 2 min |
| Flow Rate | 1 mL/min |
| Wavelength | 220 |
| Solvent Pair | Water-Methanol-TFA |
| Column | PHENOMENEX-LUNA 2.0 × 30 mm 3 um |

General Procedure to Prepare Claim I from Esters:

[Structure of methyl ester derivative] and/or [Structure of ethyl ester derivative] →

[Structure of carboxylic acid product]

K₂CO₃ (2 eq.) was added into a solution of methyl ester derivative and/or ethyl ester derivative (1 eq.) in EtOH and water. The reaction was stirred at room temperature for 16 hours before solid was removed via filtration. The filtrate was purified by preparative HPLC system.

Compound 1012

| MS (M + H)⁺ Calcd. | 785.3 |
|---|---|
| MS (M + H)⁺ Observ. | 785.3 |
| Retention Time | 2.45 min |
| LC Condition | |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 2 min |
| Flow Rate | 1 mL/min |
| Wavelength | 220 |
| Solvent Pair | Water-Methanol-TFA |
| Column | PHENOMENEX-LUNA 2.0 × 30 mm 3 um |

Compound 1015

| MS (M + H)⁺ Calcd. | 809.3 |
|---|---|
| MS (M + H)⁺ Observ. | 809.4 |
| Retention Time | 2.04 min |
| LC Condition | |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 2 min |
| Flow Rate | 1 mL/min |
| Wavelength | 220 |
| Solvent Pair | Water-Methanol-TFA |
| Column | PHENOMENEX-LUNA 2.0 × 30 mm 3 um |

Compound 1016

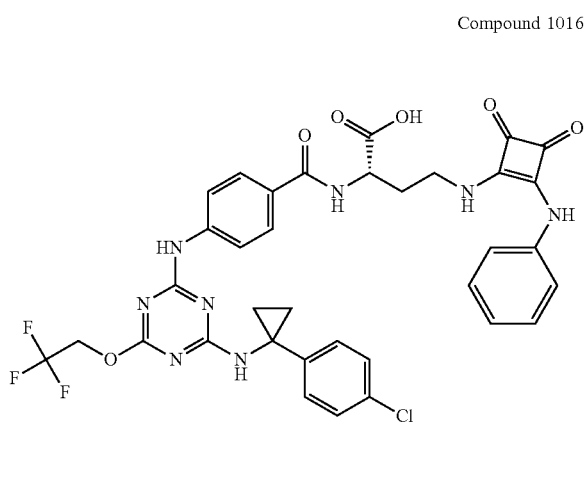

| | |
|---|---|
| MS (M + H)+ Calcd. | 751.2 |
| MS (M + H)+ Observ. | 751.3 |
| Retention Time | 2.29 min |

| LC Condition | |
|---|---|
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 2 min |
| Flow Rate | 1 mL/min |
| Wavelength | 220 |
| Solvent Pair | Water-Methanol-TFA |
| Column | PHENOMENEX-LUNA 2.0 × 30 mm 3 um |

Compound 1017

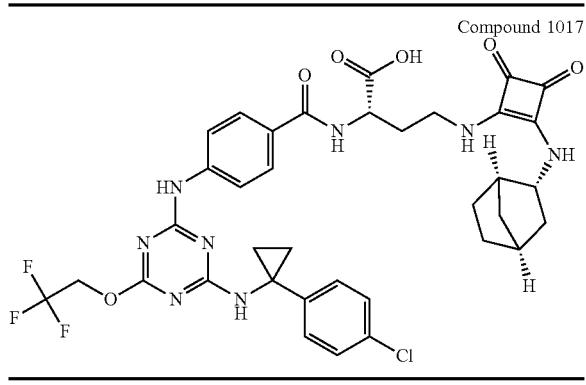

| | |
|---|---|
| MS (M + H)+ Calcd. | 769.2 |
| MS (M + H)+ Observ. | 769.5 |
| Retention Time | 1.53 min |

| LC Condition | |
|---|---|
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 2 min |
| Flow Rate | 1 mL/min |

-continued

Compound 1017

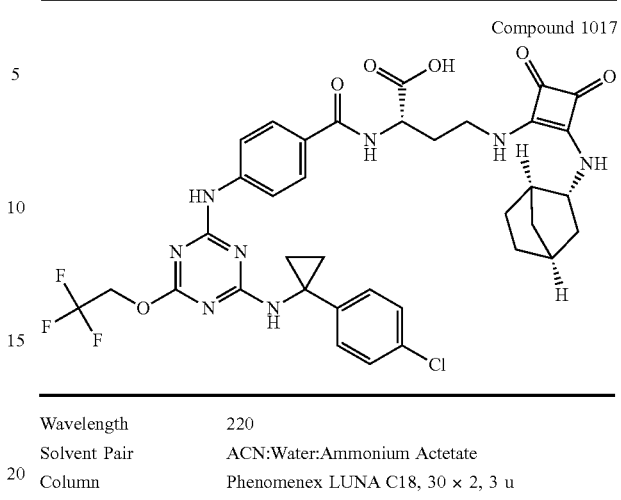

| | |
|---|---|
| Wavelength | 220 |
| Solvent Pair | ACN:Water:Ammonium Actetate |
| Column | Phenomenex LUNA C18, 30 × 2, 3 u |

Biological Methods

Infection assays. HCV pseudoparticles, produced using standardized methodology (Bartosch, B., Dubuisson, J. and Cosset, F.-L. *J. Exp. Med.* 2003, 197:633-642) were made via a liposome-based transfection procedure of 293T cells with plasmids expressing the murine leukemia virus capsid and polymerase proteins, an MLV genome encoding the luciferase reporter gene, and envelope glycoproteins from either HCV or vesicular stomatitis virus (VSV). The genotype 1a HCV E1 and E2 envelope coding sequences were derived from the H77C isolate (GenBank accession number AF009606). Media containing pseudoparticles was collected 3 days following transfection, filtered, and stored at −20° C. as a viral stock. Infections were performed in 384-well plates by mixing pseudovirus with $1\times10^4$ Huh7 cells/well in the presence or absence of test inhibitors, followed by incubation at 37° C. Luciferase activity, reflecting the degree of entry of the pseudoparticles into host cells, was measured 2 days after infection. The specificity of the compounds for inhibiting HCV was determined by evaluating inhibition of VSV pseudoparticle infection.

Compounds and data analysis. Test compounds were serially diluted 3-fold in dimethyl sulfoxide (DMSO) to give a final concentration range in the assay of 50.0 μM to 0.04 pM. Maximum activity (100% of control) and background were derived from control wells containing DMSO but no inhibitor or from uninfected wells, respectively. The individual signals in each of the compound test wells were then divided by the averaged control values after background subtraction and multiplied by 100% to determine percent activity. Assays were performed in duplicate and average $EC_{50}$ values (reflecting the concentration at which 50% inhibition of virus replication was achieved) were calculated. Compound $EC_{50}$ data is expressed as A=0.01≤10 nM; B=10-1000 nM. Representative data for compounds are reported in Table 2.

TABLE 2

| Compd # | Structure | EC$_{50}$ (1a, nM) | EC$_{50}$ (1a, nM) |
|---|---|---|---|
| 1001 | 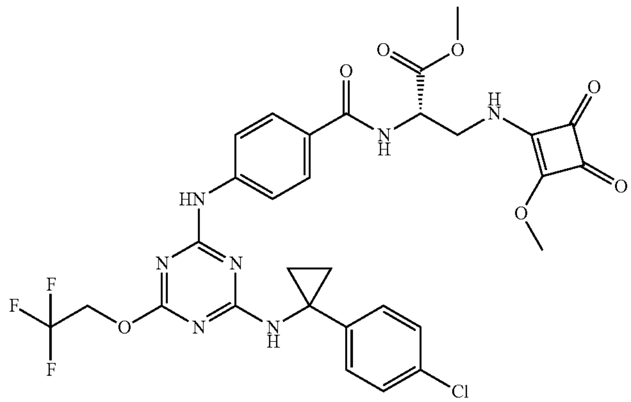 [SMILES: COC(=O)[C@H](CNc1c(OC)c(=O)c1=O)NC(=O)c1ccc(Nc2nc(NC3(c4ccc(Cl)cc4)CC3)nc(OCC(F)(F)F)n2)cc1] | 117.20 | B |
| 1002 | 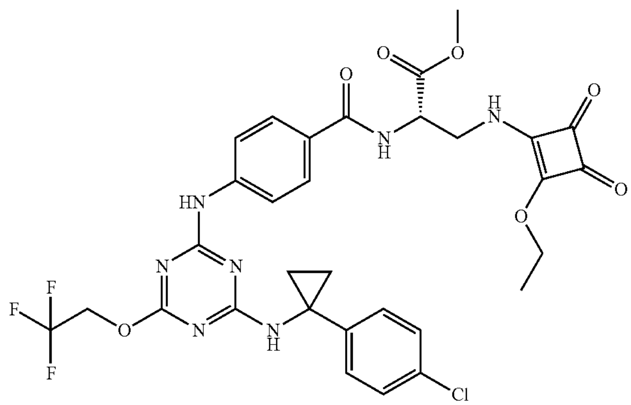 [SMILES: CCOc1c(NC[C@H](NC(=O)c2ccc(Nc3nc(NC4(c5ccc(Cl)cc5)CC4)nc(OCC(F)(F)F)n3)cc2)C(=O)OC)c(=O)c1=O] | | B |
| 1003 | 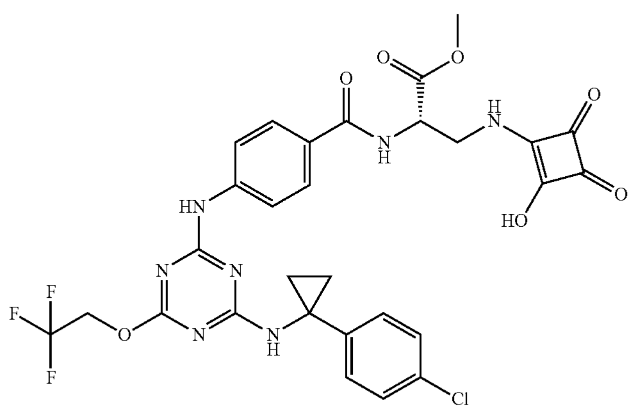 [SMILES: COC(=O)[C@H](CNc1c(O)c(=O)c1=O)NC(=O)c1ccc(Nc2nc(NC3(c4ccc(Cl)cc4)CC3)nc(OCC(F)(F)F)n2)cc1] | 47.00 | B |
| 1004 | 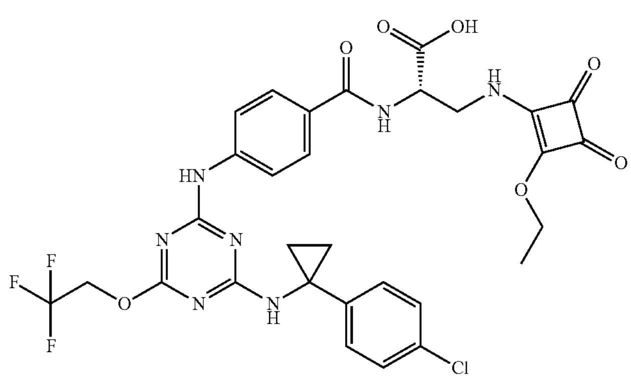 [SMILES: CCOc1c(NC[C@H](NC(=O)c2ccc(Nc3nc(NC4(c5ccc(Cl)cc5)CC4)nc(OCC(F)(F)F)n3)cc2)C(=O)O)c(=O)c1=O] | | B |

TABLE 2-continued

| Compd # | Structure | EC$_{50}$ (1a, nM) | EC$_{50}$ (1a, nM) |
|---|---|---|---|
| 1005 | 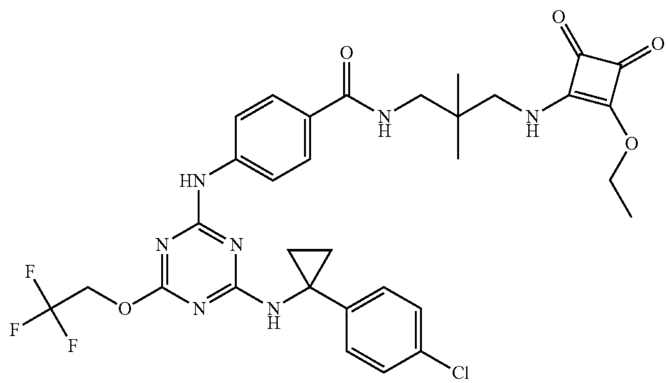 [SMILES: CCOc1c(NCC(C)(C)CNC(=O)c2ccc(Nc3nc(NC4(c5ccc(Cl)cc5)CC4)nc(OCC(F)(F)F)n3)cc2)c(=O)c1=O] | | A |
| 1006 | 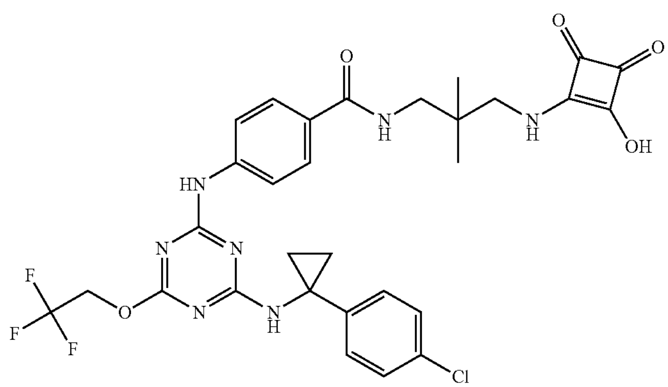 [SMILES: CC(C)(CNC(=O)c1ccc(Nc2nc(NC3(c4ccc(Cl)cc4)CC3)nc(OCC(F)(F)F)n2)cc1)CNc1c(O)c(=O)c1=O] | 0.52 | A |
| 1007 | 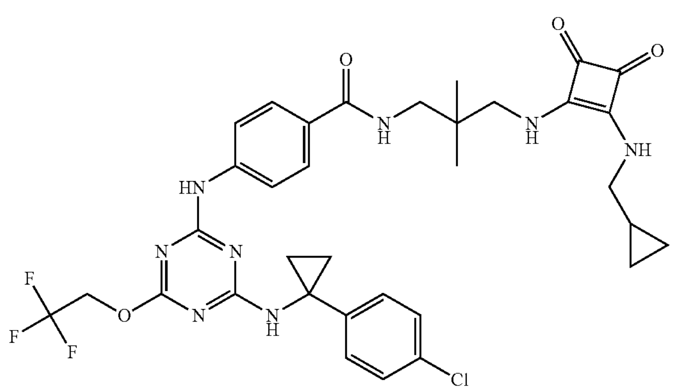 [SMILES: CC(C)(CNC(=O)c1ccc(Nc2nc(NC3(c4ccc(Cl)cc4)CC3)nc(OCC(F)(F)F)n2)cc1)CNc1c(NCC2CC2)c(=O)c1=O] | | A |
| 1008 | 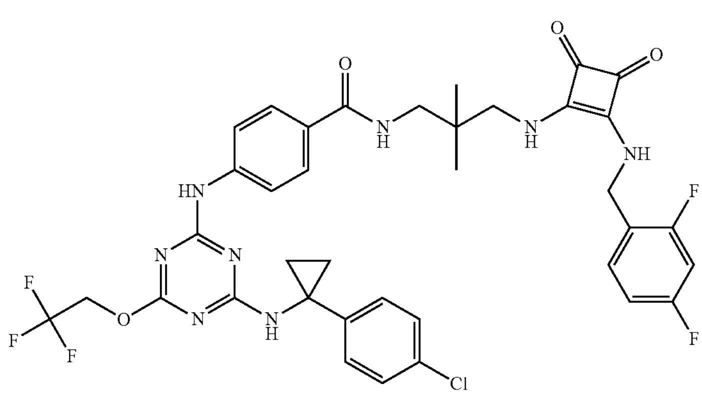 [SMILES: CC(C)(CNC(=O)c1ccc(Nc2nc(NC3(c4ccc(Cl)cc4)CC3)nc(OCC(F)(F)F)n2)cc1)CNc1c(NCc2ccc(F)cc2F)c(=O)c1=O] | 0.050 | A |

TABLE 2-continued

| Compd # | Structure | EC$_{50}$ (1a, nM) | EC$_{50}$ (1a, nM) |
|---|---|---|---|
| 1009 | 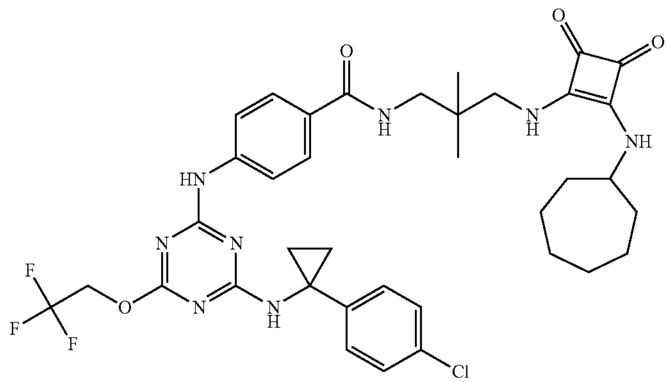 [SMILES: CC(C)(CNC(=O)c1ccc(Nc2nc(NC3(c4ccc(Cl)cc4)CC3)nc(OCC(F)(F)F)n2)cc1)CNc1c(NC2CCCCCC2)c(=O)c1=O] | | A |
| 1010 | 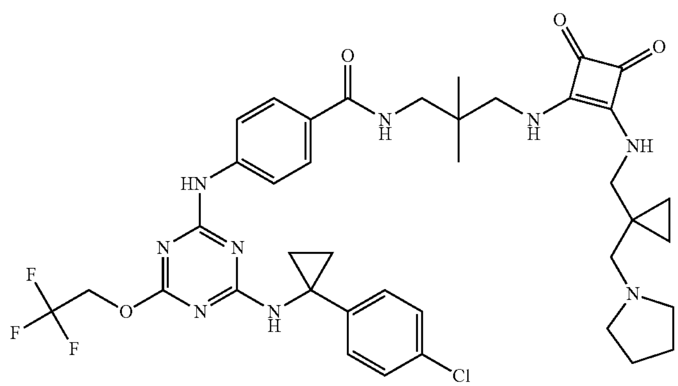 [SMILES: CC(C)(CNC(=O)c1ccc(Nc2nc(NC3(c4ccc(Cl)cc4)CC3)nc(OCC(F)(F)F)n2)cc1)CNc1c(NCC2(CN3CCCC3)CC2)c(=O)c1=O] | | A |
| 1011 | 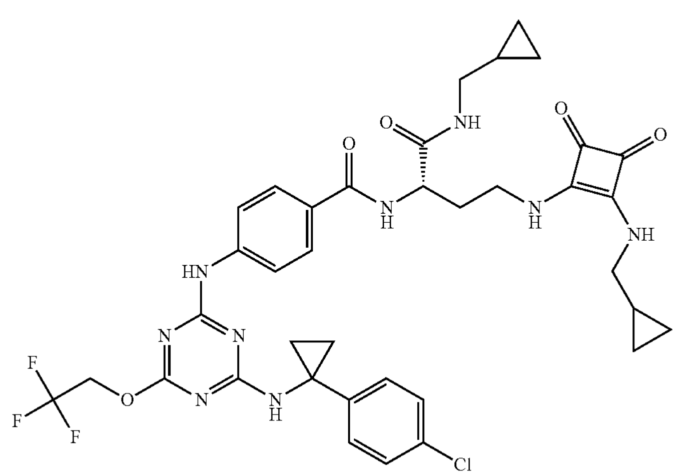 [SMILES: O=C(N[C@@H](CCNc1c(NCC2CC2)c(=O)c1=O)C(=O)NCC1CC1)c1ccc(Nc2nc(NC3(c4ccc(Cl)cc4)CC3)nc(OCC(F)(F)F)n2)cc1] | 5.98 | A |

TABLE 2-continued

| Compd # | Structure | EC$_{50}$ (1a, nM) | EC$_{50}$ (1a, nM) |
|---|---|---|---|
| 1012 | 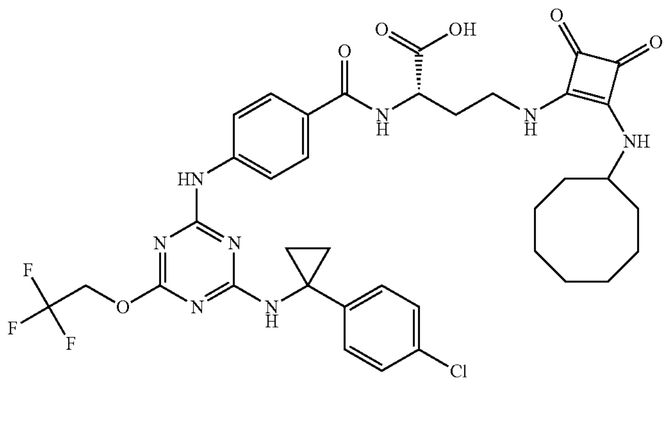 [SMILES: O=C(N[C@@H](CCNc1c(NC2CCCCCCC2)c(=O)c1=O)C(=O)O)c1ccc(Nc2nc(NC3(c4ccc(Cl)cc4)CC3)nc(OCC(F)(F)F)n2)cc1] | | A |
| 1013 | 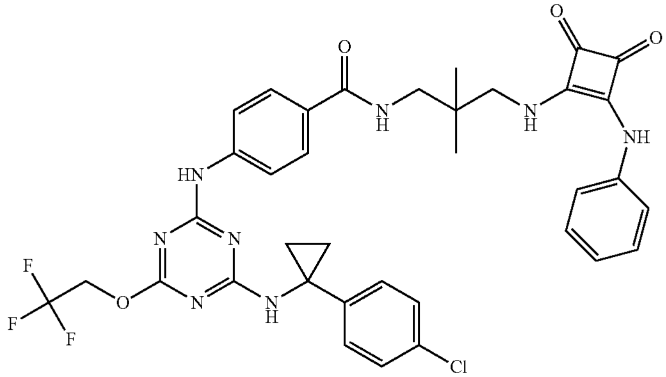 [SMILES: CC(C)(CNC(=O)c1ccc(Nc2nc(NC3(c4ccc(Cl)cc4)CC3)nc(OCC(F)(F)F)n2)cc1)CNc1c(Nc2ccccc2)c(=O)c1=O] | | A |
| 1014 | 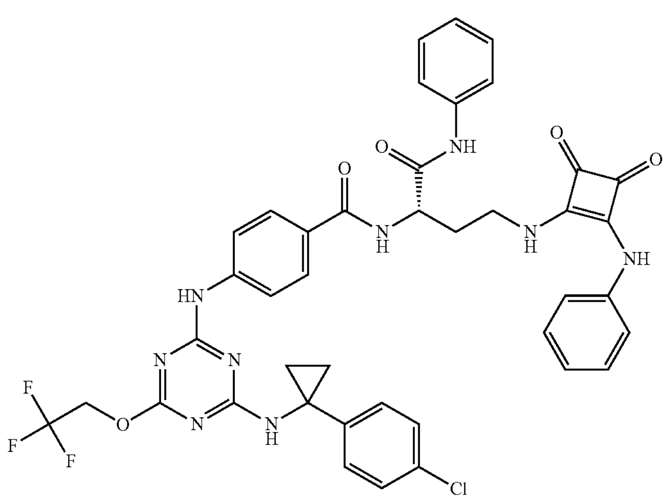 [SMILES: O=C(N[C@@H](CCNc1c(Nc2ccccc2)c(=O)c1=O)C(=O)Nc1ccccc1)c1ccc(Nc2nc(NC3(c4ccc(Cl)cc4)CC3)nc(OCC(F)(F)F)n2)cc1] | | B |

TABLE 2-continued

| Compd # | Structure | EC$_{50}$ (1a, nM) | EC$_{50}$ (1a, nM) |
|---|---|---|---|
| 1015 | 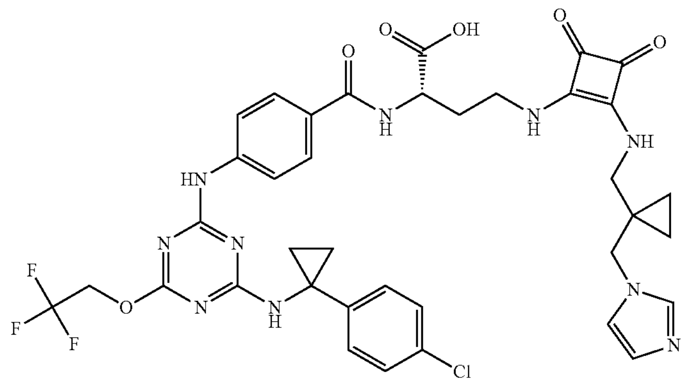 [SMILES: O=C(N[C@@H](CCNc1c(NCC2(Cn3ccnc3)CC2)c(=O)c1=O)C(=O)O)c1ccc(Nc2nc(NC3(c4ccc(Cl)cc4)CC3)nc(OCC(F)(F)F)n2)cc1] | 6.55 | A |
| 1016 | 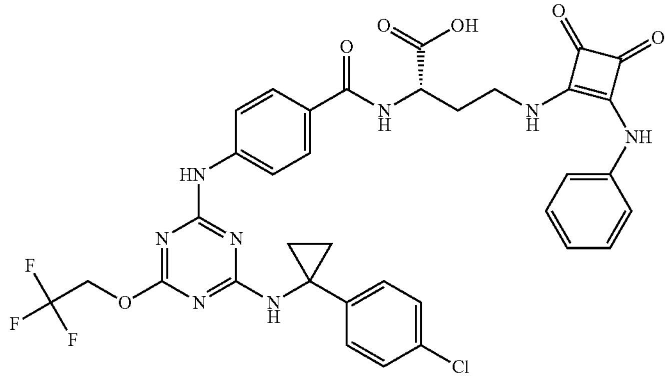 [SMILES: O=C(N[C@@H](CCNc1c(Nc2ccccc2)c(=O)c1=O)C(=O)O)c1ccc(Nc2nc(NC3(c4ccc(Cl)cc4)CC3)nc(OCC(F)(F)F)n2)cc1] | | A |
| 1017 | 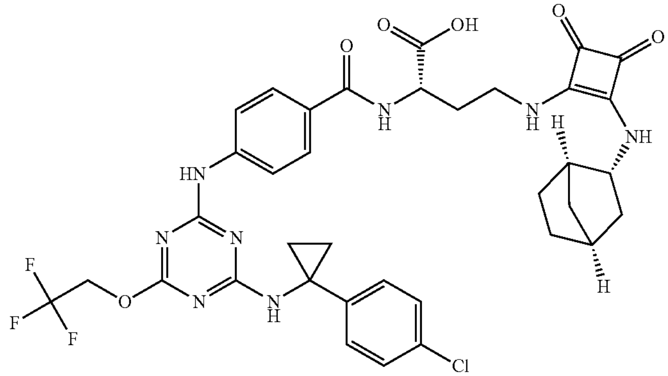 [SMILES: O=C(N[C@@H](CCNc1c(N[C@@H]2C[C@H]3CC[C@@H]2C3)c(=O)c1=O)C(=O)O)c1ccc(Nc2nc(NC3(c4ccc(Cl)cc4)CC3)nc(OCC(F)(F)F)n2)cc1] | | A |

TABLE 2-continued
| Compd # | Structure | EC$_{50}$ (1a, nM) | EC$_{50}$ (1a, nM) |
|---|---|---|---|
| 1018 | 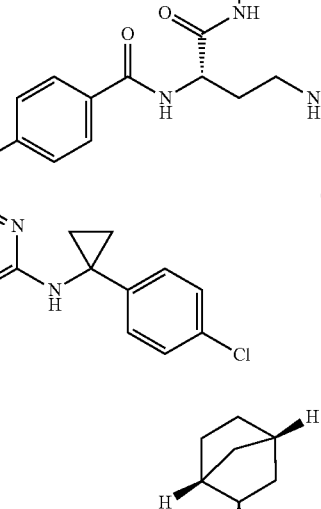 | | A |
| 1019 | 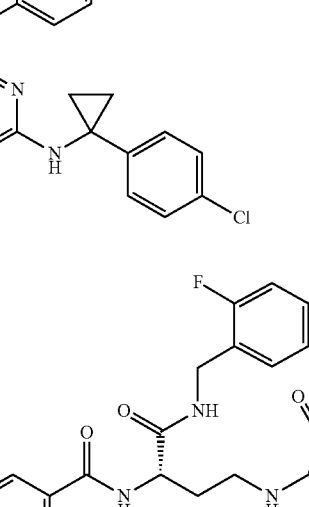 | | B |
| 1020 | 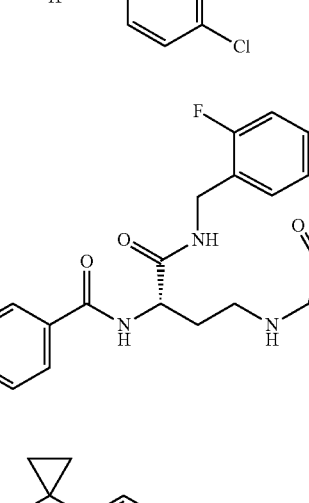 | | A |

TABLE 2-continued

| Compd # | Structure | EC$_{50}$ (1a, nM) | EC$_{50}$ (1a, nM) |
|---|---|---|---|
| 1021 | 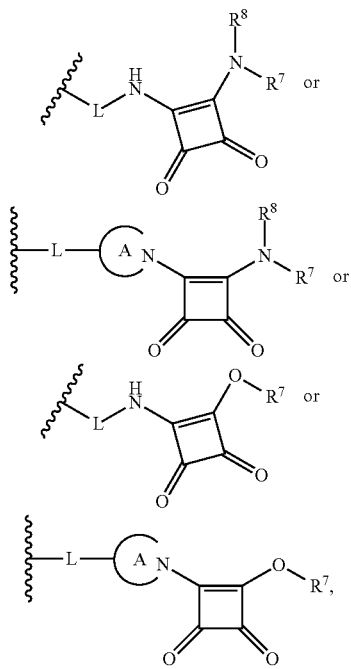 | 1.24 | A |

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

What is claimed is:

1. A compound of Formula I, or a pharmaceutically acceptable salt thereof:

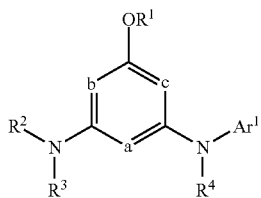

I wherein a, b and c are nitrogen;

R$^1$ is selected from alkyl, hydroxyalkyl, alkoxyalkyl, haloalkyl, cycloalkyl, hydroxycycloalkyl, alkoxycycloalkyl, halocycloalkyl, cycloalkenyl, indanyl, alkylcarbonyl, and benzyl, wherein the benzyl moiety is substituted with 0-3 substituents selected from halo, alkyl, cycloalkyl, alkenyl, alkynyl, hydroxyl, cyano, haloalkyl, alkoxy, and haloalkoxy;

R$^2$ is selected from alkyl, cycloalkyl, (Ar$^2$)alkyl, (Ar$^2$)cycloalkyl, ((Ar$^2$)cycloalkyl)alkyl, ((Ar$^2$)alkyl)cycloalkyl, and (((Ar$^2$)alkyl)cycloalkyl)alkyl;

R$^3$ is hydrogen, alkyl or cycloalkyl;

R$^4$ is hydrogen, alkyl or cycloalkyl;

R$^5$ is

<br> wherein ring A is a 4 to 7 membered alkylene ring substituted with L;

R$^6$ is selected from hydrogen, halo, alkyl, cycloalkyl, haloalkyl, halocycloalkyl, alkoxy, and haloalkoxy;

R$^7$ is hydroxy, alkyloxy, phenoxy, SO$_2$R$^9$, SO$_2$N(R$^{10}$)(R$^{11}$), CN, alkyl, cycloalkyl, benzocycloalkyl, bicyclicalkyl, (cycloalkyl)alkyl, (alkyl)cycloalkyl, ((alkyl))cycloalkyl)alkyl, or bridged bicycloalkyl, and is substituted with 0-4 substituents selected from the group consisting of halo, alkyl, cycloalkyl, benzocycloalkyl, bicyclicalkyl, hydroxyalkyl, alkoxyalkyl, hydroxy, alkoxy, benzyloxy, ether, cyclicether, benzocyclicether, bicyclicether, CO$_2$R$^9$, NR$^9$CO$_2$R$^{11}$, N(R$^{10}$)(R$^{11}$), CON(R$^{10}$)(R$^{11}$), NR$^9$CON(R$^{10}$)(R$^{11}$), SO$_2$N ($R^{10}$)($R^{11}$), tetrahydrofuranyl, tetrahydropyranyl, $Ar^3$, $OAr^3$, $NR^{13}Ar^3$, $N(R^{13})COAr^3$, $N(R^{13})COAr^3$, and $N(R^{13})SO_2Ar^3$;

or $R^7$ is hydrogen, N-alkoxycarbonylpiperidinyl, piperidinonyl, or $Ar^4$;

$R^8$ is hydrogen, alkyl, or cycloalkyl, and alkyl or cycloalkyl is substituted with 0-4 substituents selected from the group consisting of halo, alkyl, cycloalkyl, fused bicyclic alkyl, bridged bicyclic alkyl, spiro bicyclic alkyl, hydroxyalkyl, alkoxyalkyl, hydroxy, alkoxy, benzyloxy, $CO_2R^9$, $N(R^{10})$ ($R^{11}$), tetrahydrofuranyl, tetrahydropyranyl, $Ar^3$, $OAr^3$, $NR^{13}Ar^3$, $N(R^{13})COAr^3$, and $N(R^{13})SO_2Ar^3$;

or $R^7$ and $R^8$ taken together with the nitrogen to which they are attached is azetidinyl, pyrrolidinyl, piperidinyl, piperazinyl, morpholinyl, thiomorpholinyl, thiomorpholine 1,1-dioxide, tetrahydroquinolinyl, tetrahydroisoquinolinyl, indolinyl or isoindolinyl, and is substituted with 0-2 substituents selected from alkyl, (aryl) aklyl, alkylcarbonyl, and alkoxycarbonyl;

$R^9$ is hydrogen, $Ar^3$, alkyl, cycloalkyl, hydroxyalkyl, alkoxyalkyl, ((hydroxyalkyl)alkoxy)alkoxy, or ((alkoxy)alkoxy)alkoxy;

$R^{10}$ is hydrogen, alkyl, cycloalkyl, alkylcarbonyl, alkoxycarbonyl, or $Ar^6$;

$R^{11}$ is hydrogen, alkyl, cycloalkyl, or $Ar^6$;

or $R^{10}$ and $R^{11}$ taken together with the nitrogen to which they are attached is azetidinyl, pyrrolidinyl, piperidinyl, piperazinyl, morpholinyl, thiomorpholinyl, thiomorpholine 1,1-dioxide, tetrahydroquinolinyl, tetrahydroisoquinolinyl, indolinyl or isoindolinyl, and is substituted with 0-2 substituents selected from alkyl, (aryl) aklyl, alkylcarbonyl, and alkoxycarbonyl;

$R^{12}$ is hydrogen, alkyl, cycloalkyl, or $Ar^6$;

$R^{13}$ is hydrogen, alkyl, cycloalkyl, alkylcarbonyl, alkoxycarbonyl, or $Ar^6$, and is substituted with 0-3 substituents selected from cyano, halo, alkyl, alkyenyl, haloalkyl, alkoxy, and haloalkoxy, $N(R^{15})$ ($R^{16}$) and alkylCO;

$R^{14}$ is hydrogen, alkyl, cycloalkyl, or $Ar^6$;

or $R^{13}$ and $R^{14}$ taken together with the nitrogen to which they are attached is azetidinyl, pyrrolidinyl, piperidinyl, piperazinyl, morpholinyl, thiomorpholinyl, thiomorpholine 1,1-dioxide, tetrahydroquinolinyl, tetrahydroisoquinolinyl, indolinyl, or isoindolinyl, and is substituted with 0-2 substituents selected from alkyl, (aryl) aklyl, alkylcarbonyl, and alkoxycarbonyl;

$R^{15}$ is hydrogen, alkyl, cycloalkyl, alkylcarbonyl, or alkoxycarbonyl;

$R^{16}$ is hydrogen, alkyl, or cycloalkyl;

or $R^{15}$ and $R^{16}$ taken together with the nitrogen to which they are attached is azetidinyl, pyrrolidinyl, piperidinyl, piperazinyl, morpholinyl, thiomorpholinyl, thiomorpholine 1,1-dioxide, tetrahydroquinolinyl, tetrahydroisoquinolinyl, indolinyl, or isoindolinyl, and is substituted with 0-2 substituents selected from alkyl, (aryl) aklyl, alkylcarbonyl, and alkoxycarbonyl;

L is selected from the group of alkylene, cycloalkylene, (cycloalkyl)alkyl, (alkyl)cycloalkyl, and alkyl(cycloalkyl)alkyl, and is substituted with 0-1 $CO_2R^{12}$ or $CONR^{13}R^{14}$;

$Ar^1$ is phenyl or pyridyl or pyrimidinyl or pyrazolyl, substituted with 1 $CON(R^5)(R^6)$ and with 0-3 substituents selected from halo, alkyl, haloalkyl, alkoxy, and haloalkoxy;

$Ar^2$ is phenyl substituted with 0-3 substituents selected from halo, hydroxy, cyano, alkyl, cycloalkyl, alkenyl, alkynyl, haloalkyl, alkoxy, and haloalkoxy;

$Ar^3$ is phenyl, biphenyl, terphenyl, naphthalenyl, furanyl, benzofuranyl, fluorenyl, fluorenonyl, thiophenyl, benzothiophenyl, pyrrolyl, indolyl, indanyl, pyridinyl, quinolinyl, azaquinolinyl, isoquinolinyl, azaisoquinolinyl, quinoxalinyl, azaquinoxalinyl, pyrimidinyl, quinazolinyl, azaquinazolinyl, pyrazolyl, indazolyl, azaindolyl, oxazolyl, benzoxazolyl, azabenzoxazolyl, isoxazolyl, benzoisoxazolyl, azabenzoisoxazolyl, imidazolyl, benzoimidazolyl, azabenzoimidazolyl, thiazolyl, benzothiazolyl, azabenzothiazolyl, isothiazolyl, benzoisothiazolyl, azabenzoisothiazolyl, oxadiazolyl, thiadiazolyl, triazolyl, benzotriazolyl, azabenzotriazolyl, tetrazolyl, indolinyl, chromenonyl, or dibenzofuranyl, and is substituted with 0-5 substituents selected from cyano, halo, alkyl, cycloalkyl, alkenyl, alkynyl, haloalkyl, cycloalkyl, ($CO_2R^{12}$)alkyl, ($CO_2R^{12}$)alkenyl, (CON($R^{13}$)($R^{14}$))alkyl, phenyl, hydroxy, alkoxy, $Ar^5$, $OAr^5$, $NR^{13}Ar^5$, $N(R^{13})COAr^5$, $N(R^{13})SO_2Ar^5$, alkylthio, haloalkoxy, haloalkylthio, alkylcarbonyl, $CO_2R^{12}$, $COR^{12}$, $SO_2R^{12}$, $CON(R^{13})(R^{14})$, $SO_2N(R^{13})(R^{14})$, $N(R^{13})(R^{14})$, amidine, urea, ketone, sulfone, sulfamide, and $PhCONHSO_2$; and said alkyl, alkenyl, cycloalkyl, alkynyl or $Ar^5$ is further substituted with 0-5 substituents selected from cyano, halo, alkyl, cycloalkyl, alkenyl, alkynyl, haloalkyl, cycloalkyl, ($CO_2R^{12}$)alkyl, ($CO_2R^{12}$)alkenyl, ($CON(R^{13})(R^{14})$)alkyl, phenyl, hydroxy, alkoxy, aryoxy, alkylthio, haloalkoxy, haloalkylthio, alkylcarbonyl, $CO_2R^{12}$, $COR^{12}$, $SO_2R^{12}$, $CON(R^{13})(R^{14})$, $SO_2N(R^{13})(R^{14})$, $N(R^{13})(R^{14})$, amidine, urea, ketone, sulfone, sulfamide, $PhCONHSO_2$ and $Ar^6$;

or $Ar^3$ is phenyl substituted with 1 substituent selected from benzyl, phenoxy, pyridyloxy, pyrimidyloxy, tetrazolyloxy, thiazolyl, phenylpyrazolyl, methyloxadiazolyl, thiadiazolyl, triazolyl, methyltriazolyl, tetrazolyl, pyridinyl, dimethoxypyrimdinyl, indolyl, indolinyl, and isoindolinyl;

$Ar^4$ is phenyl, indanyl, tetrahydronaphthyl, isochromanyl, benzodioxolyl, pyridinyl, pyrazolyl, imidazolyl, or triazolyl, and is substituted with 0-3 substituents selected from cyano, halo, alkyl, alkyenyl, haloalkyl, alkoxy, and haloalkoxy, $N(R^{13})(R^{14})$, and alkylCO;

$Ar^5$ is phenyl, naphthalenyl, furanyl, benzofuranyl, azabenzofuranyl, thiophenyl, benzothiophenyl, azabenzothiophenyl, pyrrolyl, indolyl, azaindolyl, indanyl, pyridinyl, quinolinyl, azaquinolinyl, isoquinolinyl, azaisoquinolinyl, quinoxalinyl, azaquinoxalinyl, pyrimidinyl, quinazolinyl, azaquinazolinyl, pyrazolyl, indazolyl, azaindazolyl, oxazolyl, benzoxazolyl, azabenzoxazolyl, isoxazolyl, benzoisoxazolyl, azabenzoisoxazolyl, imidazolyl, benzoimidazolyl, azabenzoimidazolyl, thiazolyl, benzothiazolyl, azabenzothiazolyl, isothiazolyl, benzoisothiazolyl, azabenzothiazolyl, oxadiazolyl, thiadiazolyl, triazolyl, benzotriazolyl, azabenzotriazolyl, tetrazolyl, or indolinyl, and is substituted with 0-5 substituents selected from cyano, halo, alkyl, cycloalkyl, alkenyl, alkynyl, haloalkyl, cycloalkyl, ($CO_2R^{12}$)alkyl, ($CO_2R^{12}$)alkenyl, ($CON(R^{13})(R^{14})$)alkyl, phenyl, hydroxy, alkoxy, $OAr^6$, $NR^{13}Ar^6$, alkylthio, haloalkoxy, haloalkylthio, alkylcarbonyl, $CO_2R^{12}$, $COR^{12}$, $SO_2R^{12}$, $CON(R^{13})(R^{14})$, $SO_2N(R^{13})(R^{14})$, $N(R^{13})(R^{14}$ amidine, urea, ketone, sulfone and sulfamide;

Ar⁶ is phenyl, naphthalenyl, furanyl, benzofuranyl, azabenzofuranyl, thiophenyl, benzothiophenyl, azabenzothiophenyl, pyrrolyl, indolyl, azaindolyl, indanyl, pyridinyl, quinolinyl, azaquinolinyl, isoquinolinyl, azaisoquinolinyl, quinoxalinyl, azaquinoxalinyl, pyrimidinyl, quinazolinyl, azaquinazolinyl, pyrazolyl, indazolyl, azaindazolyl, oxazolyl, benzoxazolyl, azabenzoxazolyl, isoxazolyl, benzoisoxazolyl, azabenzoisoxazolyl, imidazolyl, benzoimidazolyl, azabenzoimidazolyl, thiazolyl, benzothiazolyl, azabenzothiazolyl, isothiazolyl, benzoisothiazolyl, azabenzothiazolyl, oxadiazolyl, thiadiazolyl, triazolyl, benzotriazolyl, azabenzotriazolyl, tetrazolyl, or indolinyl, and is substituted with 0-5 substituents selected from cyano, halo, alkyl, cycloalkyl, alkenyl, alkynyl, haloalkyl, cycloalkyl, phenyl, hydroxy, alkoxy, aryloxy, alkylthio, haloalkoxy, haloalkylthio, alkylcarbonyl, ester, ketone, amidine, urea, ketone, sulfone and sulfamide.

2. A compound, or a pharmaceutically acceptable salt thereof, which is selected from the group of

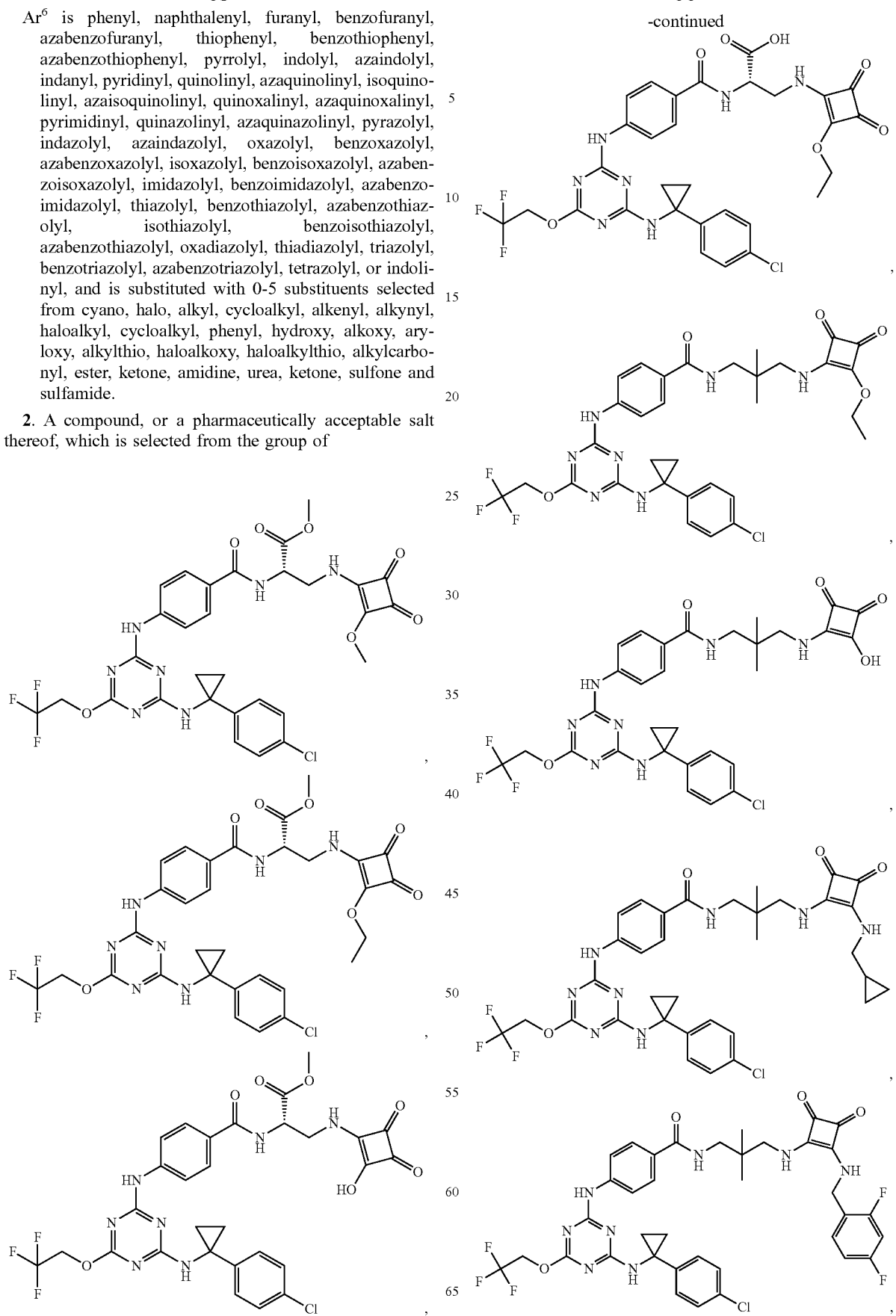

67
-continued
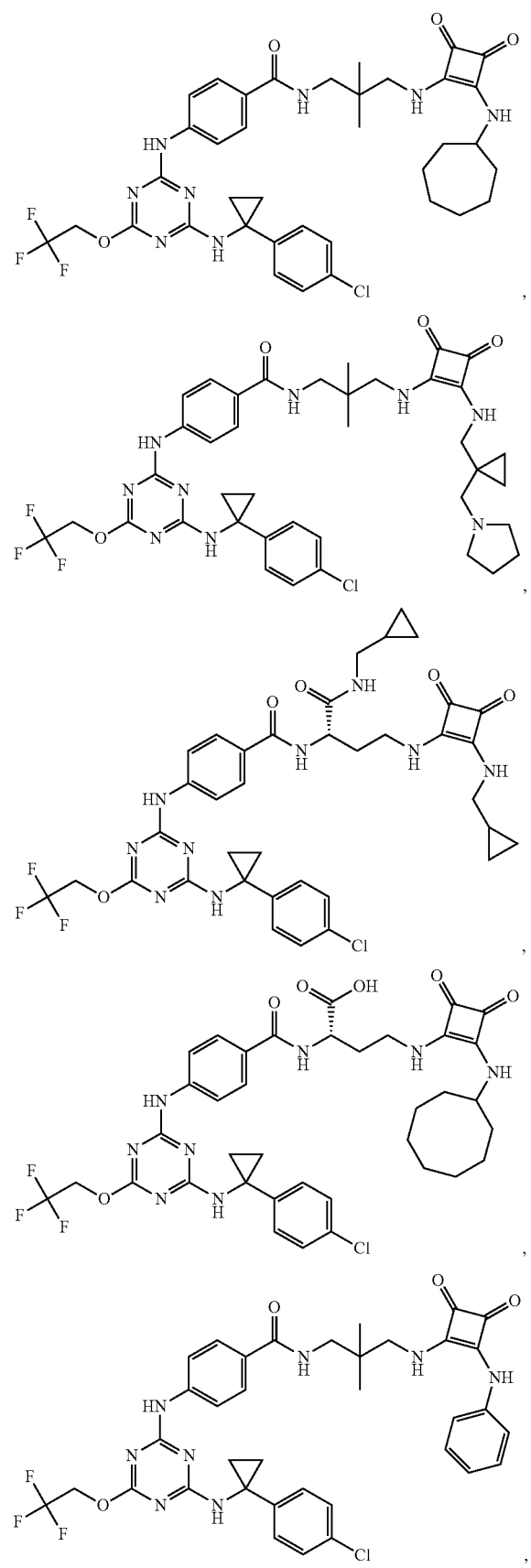
68
-continued
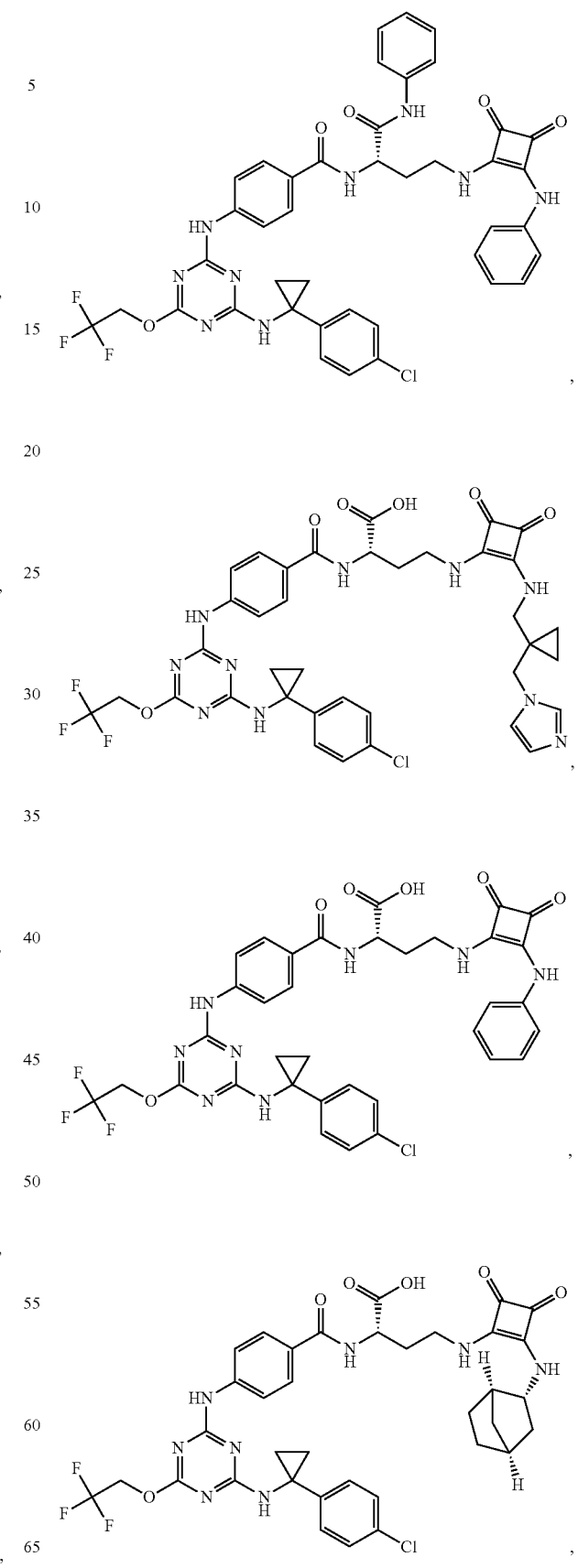

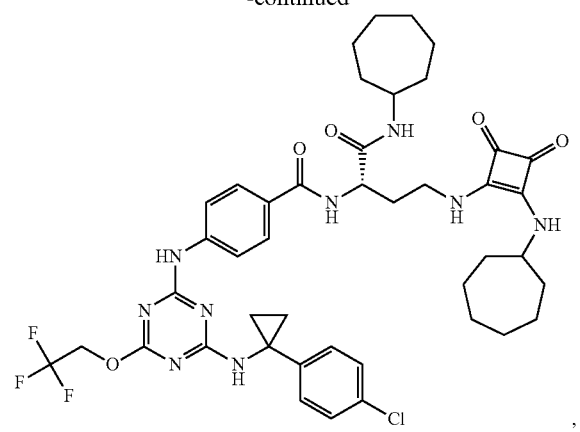
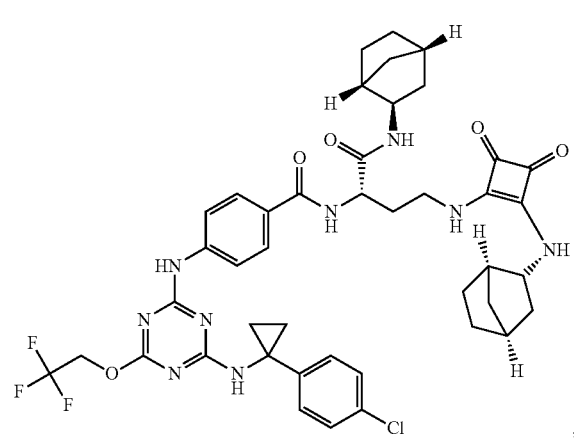
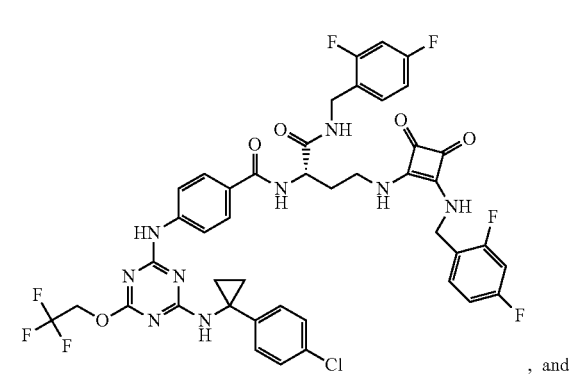
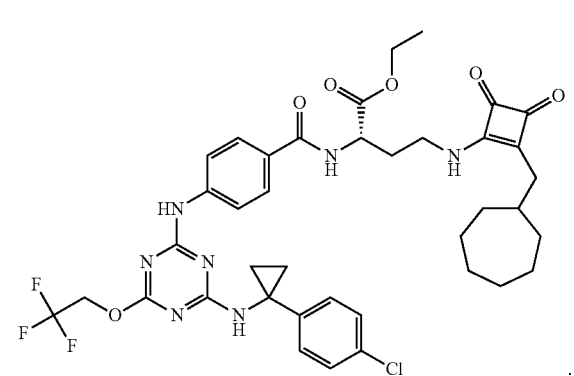 [SMILES: CCOC(=O)[C@H](CCNc1c(CC2CCCCCC2)c(=O)c1=O)NC(=O)c1ccc(Nc2nc(NC3(c4ccc(Cl)cc4)CC3)nc(OCC(F)(F)F)n2)cc1]
, and
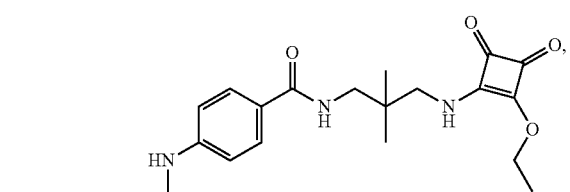
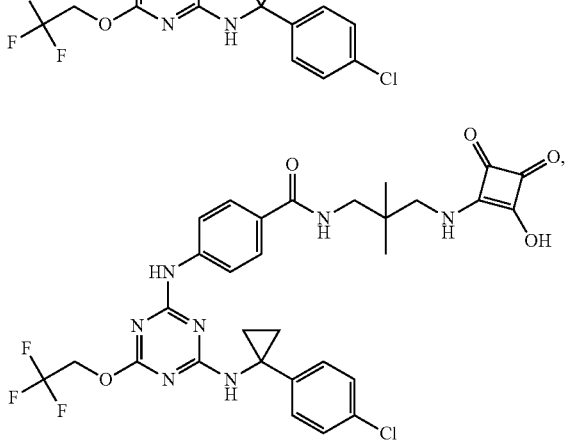
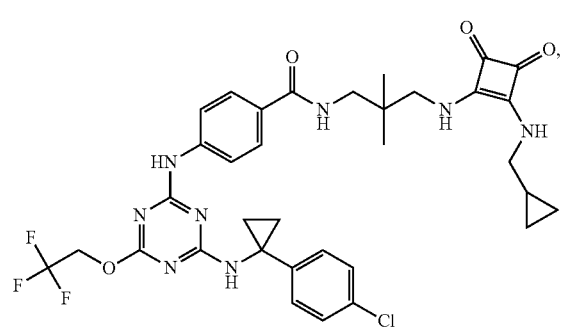
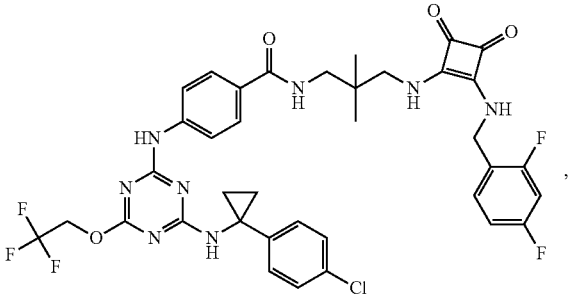
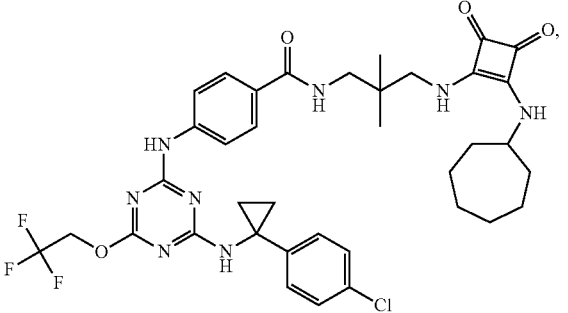
3. A compound, or a pharmaceutically acceptable salt thereof, which is selected from the group of 71
-continued
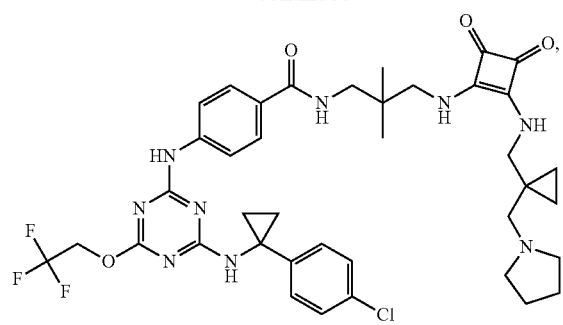
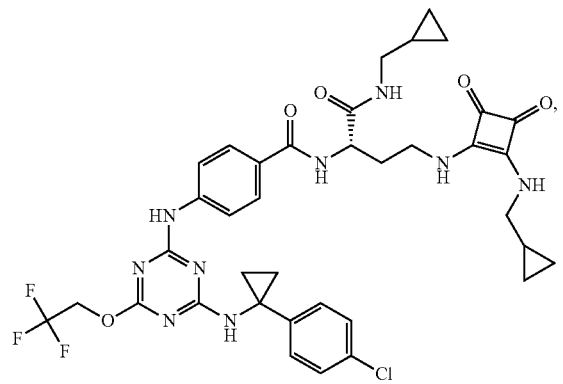
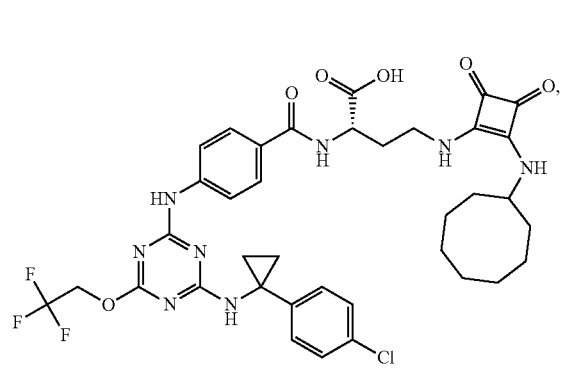
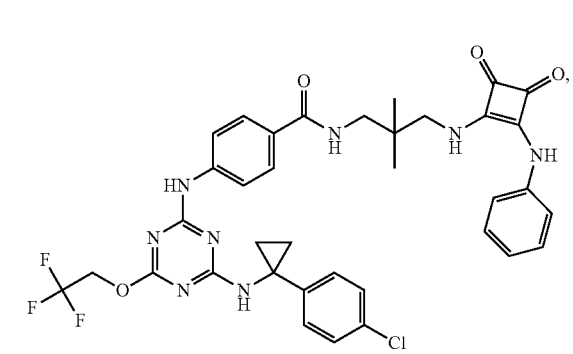
72
-continued
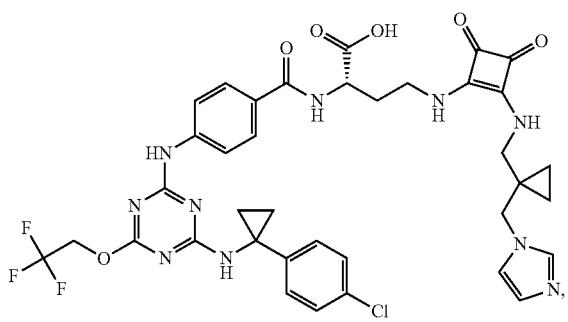
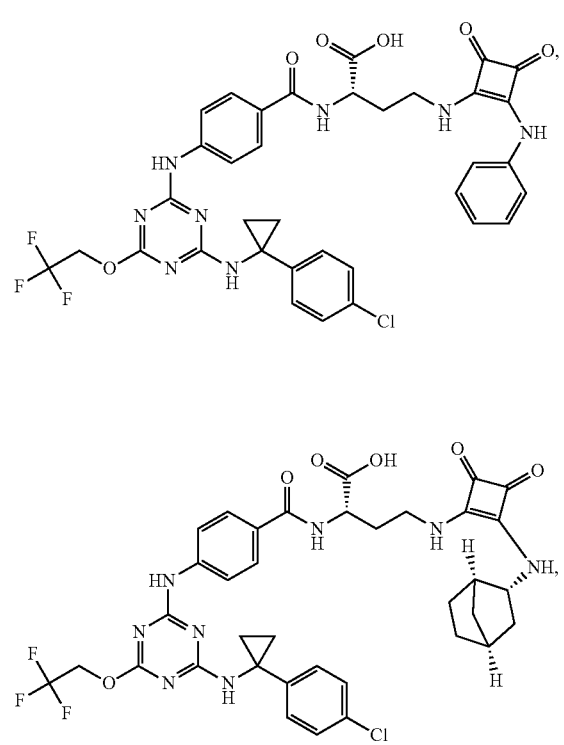
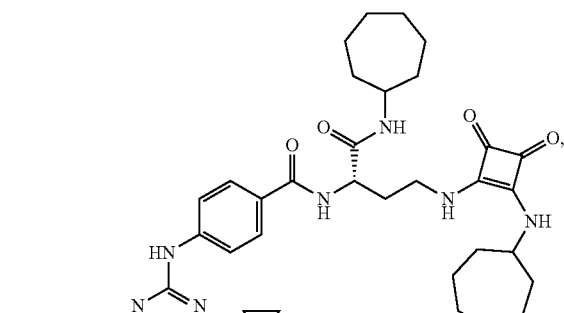

-continued

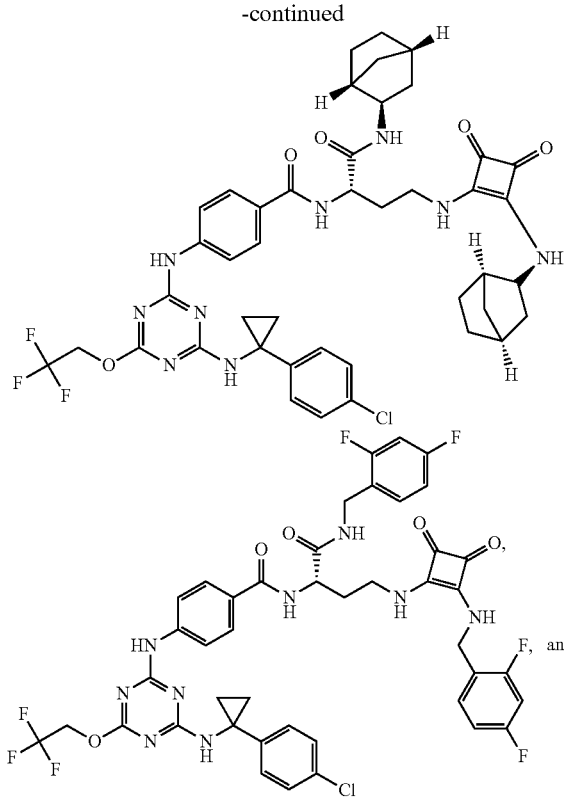

-continued

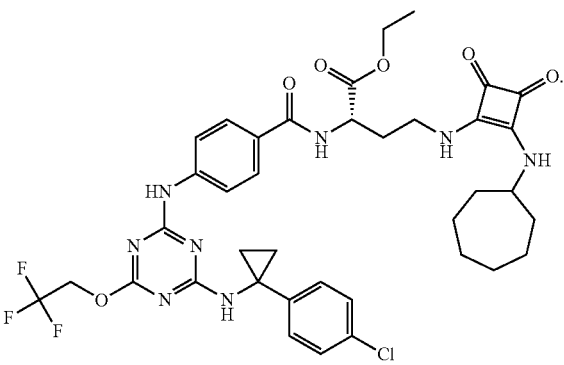

4. A composition comprising a compound of claim 1, and a pharmaceutically acceptable carrier.

5. A composition comprising a compound of claim 2, and a pharmaceutically acceptable carrier.

6. A composition comprising a compound of claim 3, and a pharmaceutically acceptable carrier.

7. A method of treating hepatitis C infection comprising administering a therapeutically effective amount of a compound of claim 1 to a patient.

* * * * *

UNITED STATES PATENT AND TRADEMARK OFFICE
CERTIFICATE OF CORRECTION

Page 1 of 2

PATENT NO. : 9,624,180 B2
APPLICATION NO. : 14/762554
DATED : April 18, 2017
INVENTOR(S) : Wang et al.

It is certified that error appears in the above-identified patent and that said Letters Patent is hereby corrected as shown below:

In the Claims

Claim 1, Column 61, Line 54:
Delete "$R^1$is" and insert -- $R^1$ is --.

Claim 1, Column 63, Line 12:
Delete "$N(R^{10})$ $(R^{11})$," and insert -- $N(R^{10})(R^{11})$, --.

Claim 1, Column 63, Lines 20-21:
Delete "(aryl)aklyl," and insert -- (aryl)alkyl, --.

Claim 1, Column 63, Lines 25:
Delete "$R^{10}$is" and insert -- $R^{10}$ is --.

Claim 1, Column 63, Line 27:
Delete "$R^{11}$is" and insert -- $R^{11}$ is --.

Claim 1, Column 63, Line 28:
Delete "$R^{10}$and $R^{11}$taken" and insert -- $R^{10}$ and $R^{11}$ taken --.

Claim 1, Column 63, Lines 34-35:
Delete "(aryl)aklyl," and insert -- (aryl)alkyl, --.

Claim 1, Column 63, Line 36:
Delete "$R^{12}$is" and insert -- $R^{12}$ is --.

Claim 1, Column 63, Line 37:
Delete "$R^{13}$is" and insert -- $R^{13}$ is --.

Signed and Sealed this
Twenty-fifth Day of September, 2018

Andrei Iancu
*Director of the United States Patent and Trademark Office*

CERTIFICATE OF CORRECTION (continued)
U.S. Pat. No. 9,624,180 B2

Claim 1, Column 63, Line 40:
Delete "$N(R^{15})$ $(R^{16})$," and insert -- $N(R^{15})(R^{16})$, --.

Claim 1, Column 63, Line 42:
Delete "$R^{14}$is" and insert -- $R^{14}$ is --.

Claim 1, Column 63, Line 43:
Delete "$R^{13}$and $R^{14}$taken" and insert -- $R^{13}$ and $R^{14}$ taken --.

Claim 1, Column 63, Lines 48-49:
Delete "(aryl)aklyl," and insert -- (aryl)alkyl, --.

Claim 1, Column 63, Line 50:
Delete "$R^{15}$is" and insert -- $R^{15}$ is --.

Claim 1, Column 63, Line 52:
Delete "$R^{16}$is" and insert -- $R^{16}$ is --.

Claim 1, Column 63, Line 53:
Delete "$R^{15}$and $R^{16}$taken" and insert -- $R^{15}$ and $R^{16}$ taken --.

Claim 1, Column 63, Lines 58-59:
Delete "(aryl)aklyl," and insert -- (aryl)alkyl, --.

Claim 1, Column 63, Line 62:
Delete "$CO_2R^{12}$or" and insert -- $CO_2R^{12}$ or --.

Claim 1, Column 63, Line 64:
Delete "$Ar^1$is" and insert -- $Ar^1$ is --.

Claim 1, Column 64, Line 66:
Delete "$N(R^{13})(R^{14}$" and insert -- $N(R^{13})(R^{14})$, --.